(12) United States Patent
Venit et al.

(10) Patent No.: US 7,659,262 B2
(45) Date of Patent: *Feb. 9, 2010

(54) COMBRETASTATIN A-4 PHOSPHATE PRODRUG MONO- AND DI-ORGANIC AMINE SALTS, MONO- AND DI-AMINO ACID SALTS, AND MONO- AND DI-AMINO ACID ESTER SALTS

(75) Inventors: John J. Venit, North Brunswick, NJ (US); Mandar V. Dali, Bridgewater, NJ (US); Manisha M. Dali, Bridgewater, NJ (US); Yande Huang, Belle Mead, NJ (US); Charles E. Dahlheim, Lawrenceville, NJ (US); Ravindra W. Tejwani, Somerset, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 160 days.

This patent is subject to a terminal disclaimer.

(21) Appl. No.: 11/366,769

(22) Filed: Mar. 1, 2006

(65) Prior Publication Data

US 2007/0270617 A1 Nov. 22, 2007

Related U.S. Application Data

(60) Continuation of application No. 11/056,452, filed on Feb. 11, 2005, which is a division of application No. 10/660,439, filed on Sep. 10, 2003, now Pat. No. 6,855,702, which is a continuation of application No. 09/950,500, filed on Sep. 11, 2001, now Pat. No. 6,670,344.

(60) Provisional application No. 60/232,568, filed on Sep. 14, 2000, provisional application No. 60/251,921, filed on Dec. 7, 2000.

(51) Int. Cl.
*A01N 57/00* (2006.01)
*C07F 9/02* (2006.01)
(52) U.S. Cl. .................. 514/130; 558/194; 558/210; 558/211
(58) Field of Classification Search .......... 514/130; 558/210, 211, 194
See application file for complete search history.

(56) References Cited

U.S. PATENT DOCUMENTS 4,659,701 A 4/1987 Wuest et al. .......... 514/130

(Continued)

FOREIGN PATENT DOCUMENTS

WO WO 92/16486 10/1992

(Continued)

OTHER PUBLICATIONS

Grant et al, Grant & Hackh's Chemical Dictionary , 1987, p. 285 (2 pages ).*

(Continued)

*Primary Examiner*—Taylor Victor Oh
(74) *Attorney, Agent, or Firm*—Karen E. Flick

(57) ABSTRACT

Provided herein are novel and useful combretastatin A-4 prodrug salts that increase the solubility of combretastatin A-4, readily regenerate combretastatin A-4 in vivo under normal physiological conditions, and which produce physiologically tolerable products as a result of the regeneration of combretastatin A-4.

9 Claims, 13 Drawing Sheets

U.S. PATENT DOCUMENTS

| | | | | |
|---|---|---|---|---|
| 5,231,112 | A | | 7/1993 | Janoff et al. ................. 514/401 |
| 5,561,122 | A | * | 10/1996 | Pettit .......................... 514/130 |
| 5,674,906 | A | | 10/1997 | Hatanaka et al. ............ 514/626 |
| 6,025,507 | A | | 2/2000 | Klar et al. ..................... 303/16 |
| 6,670,344 | B2 | * | 12/2003 | Venit et al. .................. 514/130 |
| 2006/0166942 | A1 | * | 7/2006 | Venit et al. .................. 514/129 |

FOREIGN PATENT DOCUMENTS

| | | |
|---|---|---|
| WO | WO 99/35150 | 7/1999 |
| WO | WO 00/48590 | 8/2000 |
| WO | WO 00/48591 | 8/2000 |
| WO | WO 02/14329 | 2/2002 |

OTHER PUBLICATIONS

Berge et al, Journal of Pharmaceutical Sciences, vol. 66, No. 1, 1977, p. 1-18.*

Pettit, George R. "Antineoplastic agents 393. Synthesis of the trans-isomer of combretastatin A-4 prodrug" Anti-Cancer Drug Design. 1998;13:981-993.

International Search Report for International Application No. PCT/US01/28401.

* cited by examiner

COMBRETASTATIN A-4 PHOSPHATE PRODRUG MONO- AND DI-ORGANIC AMINE SALTS, MONO- AND DI-AMINO ACID SALTS, AND MONO- AND DI-AMINO ACID ESTER SALTS

RELATED APPLICATIONS

This application is a continuation application of U.S. application Ser. No. 11/056,452, filed on Feb. 11, 2005, which is a divisional of U.S. application Ser. No. 10/660,439, filed on Sep. 10, 2003 now U.S. Pat. No. 6,855,702, which is a continuation of U.S. application Ser. No. 09/950,500, filed Sep. 11, 2001 now U.S. Pat. No. 6,670,344, which claims priority from U.S. Application Ser. No. 60/232,568, filed Sep. 14, 2000, and from U.S. Application Ser. No. 60/251,921, filed Dec. 7, 2000, all of which are incorporated herein by reference in their entirety.

FIELD OF THE INVENTION

The present invention relates to novel and useful combretastatin A-4 (CA4) phosphate prodrug mono- and di-organic amine salts, mono- and di-amino acid salts, and mono- and di-amino acid ester salts, which salts have greater solubility than native combretastatin A-4, and 15 rapidly regenerate combretastatin A-4 under physiological conditions.

BACKGROUND OF THE INVENTION

Cancer is considered to be a serious and pervasive disease. The National Cancer Institute has 20 estimated that in the United States alone, 1 in 3 people will be struck with cancer during their lifetime. Moreover approximately 50% to 60% of people contracting cancer will eventually succumb to the disease. Hence, since the establishment the National Cancer Institute in the early 1970's, the amount of resources committed to cancer research has dramatically improved.

Although cancer is commonly considered to be a single disease, it actually comprises a family of diseases wherein normal cell differentiation is modified so that it becomes abnormal and uncontrolled. As a result, these malignant cells rapidly proliferate. Eventually, the cells spread or metastasize from their origin and colonize other organs, eventually killing their host. Due to the wide variety of cancers presently observed, numerous strategies have been developed to destroy cancer within the body. One such method utilizes cytotoxic chemotherapeutics. These compounds are administered to cancer sufferers with the objective of destroying malignant cells while leaving normal, healthy cells undisturbed. Particular examples of such compounds include 5-fluorouracil, cisplatin, and methotrexate.

Combretastatin A-4 was initially isolated from stem wood of the African tree *combretum caffrum* (Combretaceae), and found to be a potent inhibitor of microtubulin assembly. Moreover, combretastatin A-4 was found to be significantly active against the US National Cancer Institute's (NCI) murine L1210 and P338 lymphocytic leukemia cell lines. In addition, combretastatin A-4 was found to compete with combretastatin A-1, another compound isolated from *Combretum caffrum*, as an inhibitor of colchicine binding to tubulin. It has also been determined to retard strongly the VoLo, DLD-1 and HCT-15 human-colon cancer ($ED_{50}$<0.01 (µg/ml) cell lines, and to be one of the stronger anti-mitotic agents found among the *Combretum caffrum* constituents (U.S. Pat. No. 4,996, 237).

Consequently, research has been conducted to determine the efficacy of combretastatin A-4 as a chemotherapeutic in treating a variety of human cancers. Unfortunately, combretastatin A-4 is essentially insoluble in water. This characteristic has significantly interfered with the development of pharmaceutical compositions comprising combretastatin A-4. In order to increase its solubility as well as its efficacy, efforts have been made to create prodrug derivatives of combretastatin A-4 that will regenerate combretastatin A-4 in physiological conditions. For example, Koji Ohsumi et al. describe the synthesis of amino acid HCl prodrugs of a combretastatin analog, wherein an amino acid salt is attached to the amino group of a combretastatin derivative containing a basic amino group [the derivatives are described in Ohsumi et al, *Anti-Cancer Drug Design*, 14, 539-548 (1999)]. Although such prodrugs may have an increased solubility compared to native combretastatin A-4, they possess an inherent limitation in that the regeneration of combretastatin A-4 is dependent upon endogenous aminopeptidase in the blood of a subject to whom the prodrug is administered.

The free acid of combretastatin A-4 phosphate ("CA4P free acid") which has the following structure:

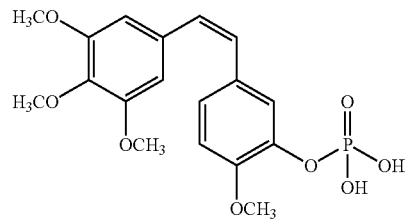

exists as an oily mass. The CA4P free acid is intrinsically Very Slightly Soluble (by USP definition) at 25° C. in water, with the aqueous solubility increasing with an increase in pH. It has two acidic groups with $pK_a$ values of 1.2 and 6.2, which are amenable to salt formation. As there are practical issues with handling CA4P free acid due to its physical state, identification of a crystalline, stable salt form of this compound is desirable.

Attempts at derivatizing combretastatin A-4 have involved forming salt derivatives of combretastatin A-4 phosphate (salt derivatives of "CA4P"). Particular examples of such salts are set forth in U.S. Pat. No. 5,561,122. Although these prodrug salts possess greater solubility than native combretastatin A-4, they can also possess inherent drawbacks, such as hygroscopicity.

Hygroscopicity is one of several important criteria in the selection of a salt. See K. Morris et al., "An Integrated Approach to the Selection of Optimal Salt Form for a New Drug Candidate", *Int. J. Pharm.*, 105, 209-217 (1994). The extent of hygroscopicity for any drug substance has significant impact on its handling and stability over the lifetime of the drug product.

Accordingly, what is needed are novel and useful combretastatin A-4 prodrug salts with favorable physiochemical properties, and which increase the solubility, and preferably efficacy, of combretastatin A-4 in treating a wide variety of neoplastic disorders.

What is also needed are novel and useful combretastatin A-4 prodrug salts which readily regenerates native combretastatin A-4 in vivo and do not produce unwanted or potentially deleterious side products when undergoing regeneration.

SUMMARY OF THE INVENTION

The citation of any reference herein should not be construed as an admission that such reference is available as "Prior Art" to the instant application.

There is provided, in accordance with the present invention, novel and useful combretastatin A-4 phosphate prodrug mono- and di-organic amine salts, mono- and di-amino acid salts, and mono- and di-amino acid ester salts, which salts have greater solubility than native combretastatin A-4, and readily regenerate combretastatin A-4 in vivo. The present invention also provides compounds which are significantly less hygroscopic than heretofore known combretastatin A-4 prodrug salts (for example, do not undergo significant changes in physical form under ambient conditions of temperature and humidity), have improved handling and stability, and which can form solutions at a pH which minimizes or eliminates pain at the injection site. The compounds of the invention thus provide considerable advantages for pharmaceutical use.

Broadly, the present invention extends to a compound having a general structure of the formula I:

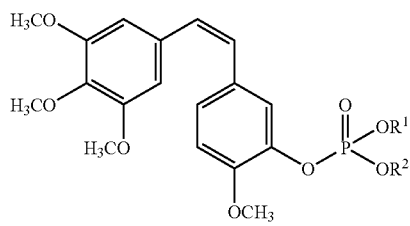

wherein one of —OR$^1$ or —OR$^2$ is —O—QH$^+$, and the other is hydroxyl or —O—QH$^+$; and Q is (A) an organic amine containing at least one nitrogen atom which, together with a proton, forms a quaternary ammonium cation QH$^+$;

(B) an amino acid containing at least two nitrogen atoms where one of the nitrogen atoms, together with a proton, forms a quaternary ammonium cation QH$^+$; or (C) an amino acid containing one or more nitrogen atoms where one of the nitrogen atoms, together with a proton, forms a quaternary ammonium cation QH$^+$ and where, further, all carboxylic acid groups of the amino acid are in the form of esters.

Throughout this specification, when both —OR$^1$ and —OR$^2$ are —O—QH$^+$, Q is preferably identical in both the —OR$^1$ and —OR$^2$ groups.

When Q has definition (A), preferred organic amine having applications herein is tromethamine (i.e., tris(hydroxymethyl)aminomethane, abbreviated herein as "TRIS").

Tromethamine salts of the formula I are illustrated by the following formulae Ia and Ib which represent the mono-tromethamine and di-tromethamine salts of formula I, respectively:

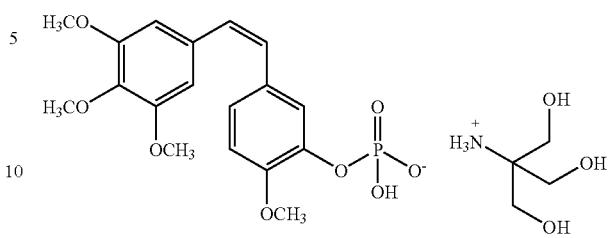

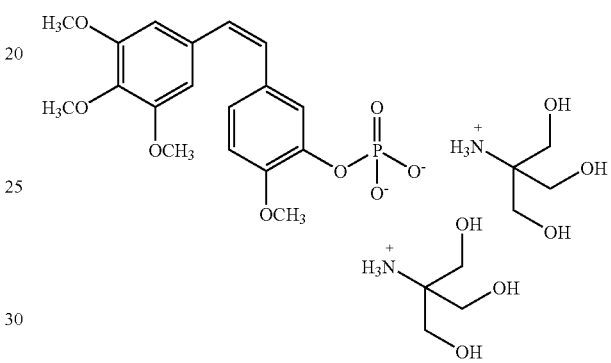

The mono-tromethamine salt of formula Ia is preferred.

When Q has definition (B), any amino acid having at least two nitrogen atoms has applications herein. Any of the nitrogens of the amino acid can form the quaternary ammonium cation of formula I, for example, any nitrogen on the amino acid side chain or the nitrogen of the α-amino group. Amino acids having applications herein include, but certainly are not limited to ornithine, histidine, lysine, arginine, tryptophan, etc.

When Q has definition (B), a preferred amino acid having applications herein is histidine. For example, either of the nitrogens of the imidazole group of the histidine side chain, or alternatively, the nitrogen of the α-amino group of histidine can form the quaternary ammonium cation of the formula I. As is readily apparent, due to the aromatic nature of the imidazole group, either of the nitrogens of the imidazole group of the histidine sidechain can form the structure of the formula (I). Preferred mono-histidine structures of the formula I are illustrated by the following formulae Ic or Id:

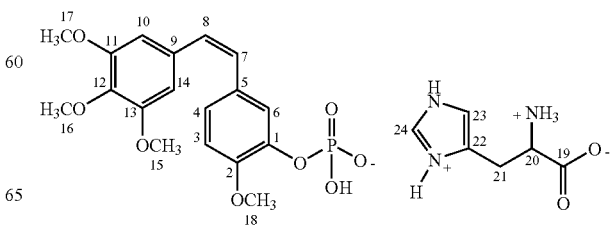

-continued

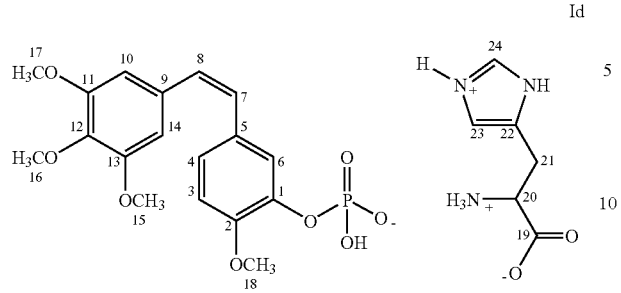

Id

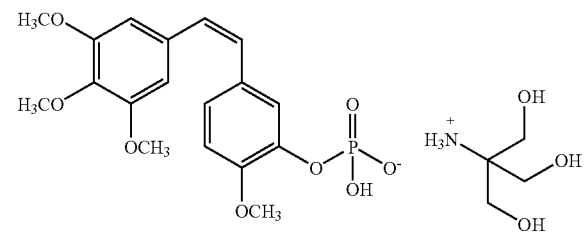

Ia

When Q has definition (C), any amino acid has applications herein, such as, but not limited to glycine. Preferred esters are alkyl esters, such as methyl or ethyl esters.

Furthermore, the present invention extends to a pharmaceutical composition comprising:

(a) a compound having a general structure of the formula I:

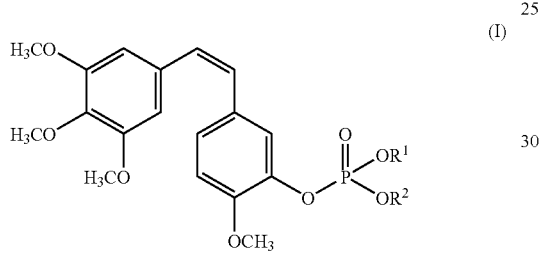

(I)

Ib wherein:
one of —OR$^1$ or —OR$^2$ is —O—QH$^+$, and the other is hydroxyl or —O—QH$^+$; and Q is (A) an organic amine containing at least one nitrogen atom which, together with a proton, forms a quaternary ammonium cation QH$^+$;

(B) an amino acid containing at least two nitrogen atoms where one of the nitrogen atoms, together with a proton, forms a quaternary ammonium cation QH$^+$; or (C) an amino acid containing one or more nitrogen atoms where one of the nitrogen atoms, together with a proton, forms a quaternary ammonium cation QH$^+$ and where, further, all carboxylic acid groups of the amino acid are in the form of esters; and (b) a pharmaceutically acceptable carrier thereof.

Particular examples of compounds of the present invention having applications in such a pharmaceutical composition are described above. Moreover, any suitable pharmaceutically acceptable carrier has applications in a pharmaceutical composition of the present invention. Particular examples are described infra. A particular embodiment of a pharmaceutical composition of the present invention comprises a compound of the present invention in which tromethamine is the organic amine, and which is preferably a tromethamine salt having the structure of formula Ia or Ib, most preferably Ia:

Another particular embodiment of a pharmaceutical composition of the present invention comprises a compound of the present invention in which histidine is the amino acid, and which is preferably a mono-histidine salt having the structure of formula Ic or Id:

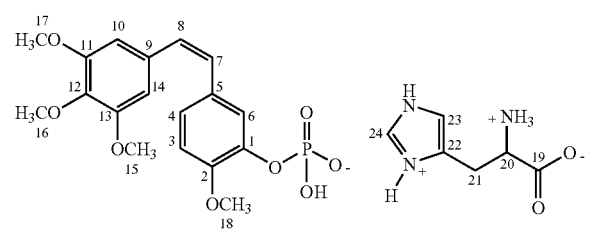

Ic

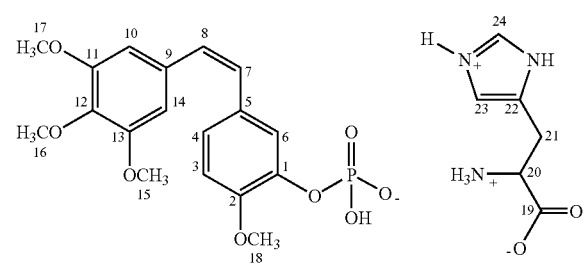

Id

Naturally, such a pharmaceutical composition would further comprise a pharmaceutically acceptable carrier thereof.

In addition, the present invention further extends to compositions comprising a salt of the present invention. In particular, a composition of the present invention can be formed by mixing compounds comprising:

(a) a CA4P free acid having the structure:

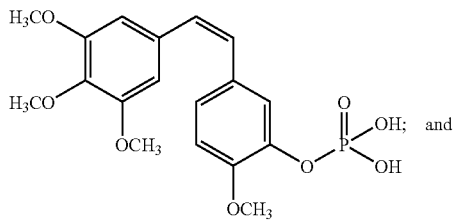

(b) a compound Q, wherein Q is (A) an organic amine containing at least one nitrogen atom which is capable of forming, together with a proton, a quaternary ammonium cation QH⁺;

(B) an amino acid containing at least two nitrogen atoms where one of the nitrogen atoms, together with a proton, forms a quaternary ammonium cation QH⁺; or (C) an amino acid containing one or more nitrogen atoms where one of the nitrogen atoms, together with a proton, forms a quaternary ammonium cation QH⁺ and where, further, all carboxylic acid groups of the amino acid are in the form of esters.

Optionally, a composition of the present invention can further comprise a pharmaceutically acceptable carrier.

Moreover, when Q has definition (A), any organic amine as defined herein has applications in a composition of the present invention. Particular examples include, but are not limited to, tromethamine, diethanolamine, glucamine, N-methylglucamine, ethylenediamine, and 2-4-imidazolyl) ethyl amine. When Q has definition (B), any amino acid having at least two nitrogen atoms has applications in a composition of the present invention. Particular examples include ornithine, histidine, lysine, arginine, tryptophan, etc. When Q has definition (C), any amino acid ester as defined herein has applications in a composition of the present invention. Particular examples include glycine.

In another embodiment, the present invention extends to a method of modulating tumor growth or metastasis in an animal comprising the administration of an amount effective therefor of a compound having a general structure of:

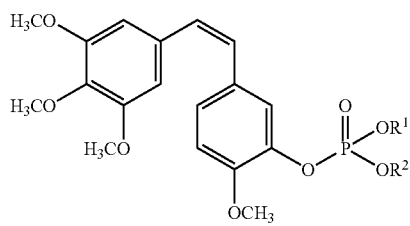

wherein:
one of —OR¹ or —OR² is —O—QH⁺, and the other is hydroxyl or —O—QH⁺; and Q is (A) an organic amine containing at least one nitrogen atom which, together with a proton, forms a quaternary ammonium cation QH⁺;

(B) an amino acid containing at least two nitrogen as where one of the nitrogen atoms, together with a proton, forms a quaternary ammonium cation QH⁺; or (C) an amino acid containing one or more nitrogen atoms where one of the nitrogen atoms, together with a proton, forms a q ammonium cation QH⁺ and where, further, all carboxylic acid groups of the amino acid are in the form of esters.

In a particular embodiment, the present invention extends to a method of modulating tumor growth or metastasis in an animal comprising the administration of an amount effective therefor of a compound in which tromethamine is the organic amine, and which is preferably a tromethamine salt having the structure of formula Ia or Ib, most preferably, Ia:

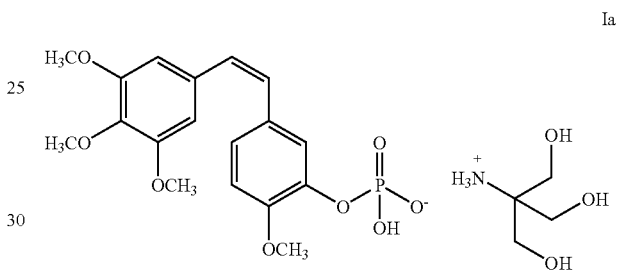

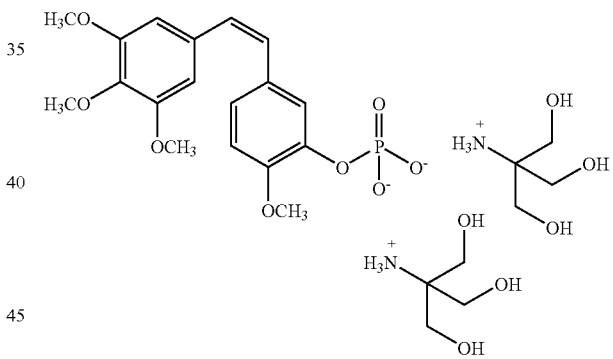

In another particular embodiment, the present invention extends to a method of modulating tumor growth or metastasis in an animal comprising the administration of an amount effective therefore of a compound in which histidine is the amino acid, and which is preferably a mono-histidine salt having the structure of formula Ic or Id:

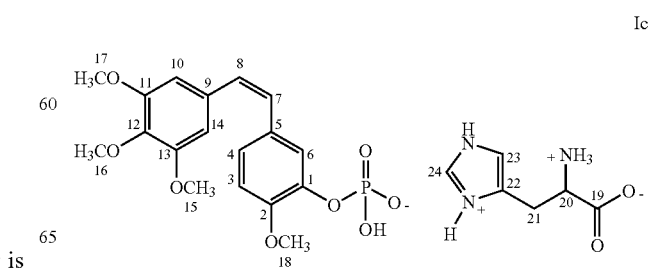

-continued

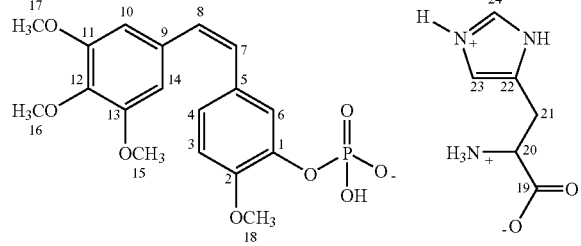

Accordingly, the present invention provides novel and useful combretastatin A4 phosphate prodrug mono- and di-organic amine salts, mono- and di-amino acid salts and mono- and di-amino acid ester salts, which salts are more soluble in aqueous solutions than native combretastatin A-4. Thus, the efficacy of this drug can be increased.

The present invention also provides combretastatin A4 phosphate prodrug mono- and di-organic amine salts, mono and di-amino acid salts and mono- and di-amino acid ester salts, which salts readily regenerate combretastatin A-4 in vivo, and which, upon dissociation, liberate an organic amine, amino acid or amino acid ester as a physiologically tolerable byproduct.

In its most preferred embodiment, the present invention provides the novel crystalline 1:1 tromethamine (TRIS) salt of the antivascular antitumor agent combretastatin A-4 phosphate prodrug having the structure of formula Ia. This compound is a phosphate ester prodrug salt, wherein the phosphate moiety undergoes dephosphorylation under physiological conditions to yield the active drug moiety, combretastatin A-4 (as mentioned below, the olefin group bridging the phenyl moieties of the core of combretastatin A-4 is in the cis configuration; the olefin group of the preferred mono TRIS salt of combretastatin A-4 phosphate is similarly in the cis configuration). The 1:1 (mono) TRIS salt of CA4P exhibits good solid-state properties and is unexpectedly practically nonhygroscopic. This and other favorable properties make the TRIS salt of CA4P a preferred compound for pharmaceutical dosage formulation.

DETAILED DESCRIPTION OF THE INVENTION

Figure 1:
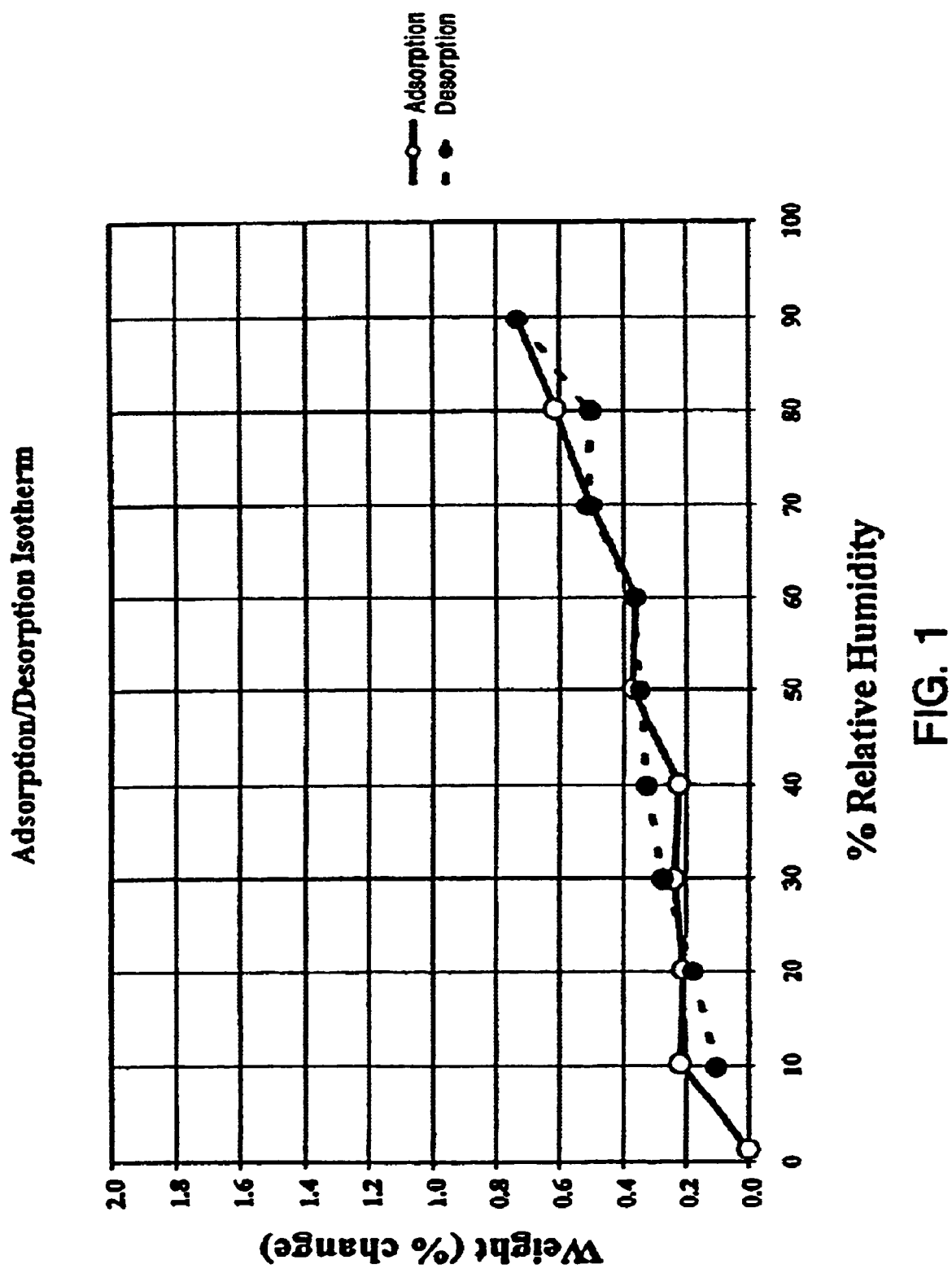
FIG. 1 shows the moisture sorption/desorption profile of the mono-TRIS salt of CA4P (prepared in Example 1) at 25° C. The data was obtained using a VTI Model MB-300W Moisture balance with relative humidity levels from 100% to 90% in increments of 10%. The maximum equilibration time at each humidity was set at 4 hours.

The present invention is based upon the discovery that surprisingly and unexpectedly, mono- and di-organic amine, mono- and di-amino acid and mono- and di-amino acid ester combretastatin A-4 phosphate prodrug salts can be formed that have increased solubility in vivo relative to the solubility of native combretastatin A-4, readily regenerate combretastatin A-4 under physiological conditions, and during regeneration, produce physiologically tolerable organic amines, or physiologically tolerable amino acids or amino acid esters that are readily metabolized in vivo.

Broadly, the present invention extends to a compound having a general structure of:

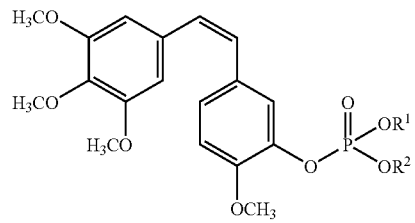

wherein:
one of —$OR^1$ or —$OR^2$ is —O—$QH^+$, and the other is hydroxyl or —O—$QH^+$; and Q is (A) an organic amine containing at least one nitrogen atom which, together with a proton, forms a quaternary ammonium cation $QH^+$;

(B) an amino acid containing at least two nitrogen atoms where one of the nitrogen atoms, together with a proton, forms a quaternary ammonium cation $QH^+$; or (C) an amino acid containing one or more nitrogen atoms where one of the nitrogen atoms, together with a proton, forms a quaternary ammonium cation QH⁺ and where, further, all carboxylic acid groups of the amino acid are in the form of esters.

All isomers of the present compounds (for example, those which may exist due to asymmetric carbons, such as on various substituents), including enantiomeric forms and diastereomeric forms, are contemplated within the scope of this invention. Individual stereoisomers of the compounds of the invention may, for example, be substantially fee of other isomers (e.g., as a pure or substantially pure optical isomer having a specified activity), or may be admixed, for example, as racemates or with all other, or other selected, stereoisomers. The chiral centers of the invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from racemates by any suitable method. The olefin group bridging the phenyl moieties of the combretastatin A-4 core is in the cis configuration, which is the preferred configuration for compounds of the present invention. Use of the terms "combretastatin A-4" or "CA4" as the name of, or part of the name of, a compound herein denotes a compound in this cis configuration. Solvates, such as hydrates, of the compound of formula I are contemplated herein.

Throughout the specification, groups and substituents may be chosen to provide stable moieties and compounds.

Embodiments indicated herein as exemplary or preferred are intended to be illustrative and not limiting.

In another embodiment, the present invention extends to a pharmaceutical composition comprising a compound of the present invention, and pharmaceutically acceptable carrier thereof. Naturally, the compounds of the present invention can be employed is any form, such as a solid or solution (particularly aqueous solution) form as is described further below. The compound, for example, can be obtained and employed in a lyophilized form alone or with suitable additives.

In yet another embodiment, the present invention extends to a method of modulating tumor growth or metastasis in an animal comprising the administration of an effective amount of a compound having a general structure of the formula I:

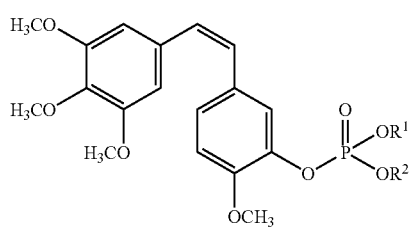

(I)

wherein:
one of —OR¹ or —OR² is —O—QH⁺, and the other is hydroxyl or —O—QH⁺; and Q is (A) an organic amine containing at least one nitrogen atom which, together with a proton, forms a quaternary ammonium cation QH⁺;

(B) an amino acid containing at least two nitrogen atoms where one of the nitrogen atoms, together with a proton, forms a quaternary ammonium cation QH⁺; or (C) an amino acid containing one or more nitrogen atoms where one of the nitrogen atoms, together with a proton, forms a quaternary ammonium cation QH⁺ and where, further, all carboxylic acid groups of the amino acid are in the form of esters.

Naturally, a compound of the present invention can be administered alone or in a pharmaceutical composition.

The terms and phrases used herein are defined below, and have the indicated definitions unless otherwise indicated.

As used herein the terms "modulate," "modulating" or "modulation" refer to changing the rate at which a particular process occurs, inhibiting a particular process, reversing a particular process, and/or preventing the initiation of a particular process. Thus, for example, where the particular process comprises tumor growth or metastasis, "modulation" of the process includes decreasing the rate at which tumor growth and/or metastasis occurs, inhibiting tumor growth and/or metastasis, reversing tumor growth and/or metastasis (including tumor shrinkage and/or eradication) and/or preventing tumor growth and/or metastasis, particularly in a subject that is prone to such a process.

As used herein, the phrase "effective amount" or "amount effective therefor" of a compound administered to an animal is that amount sufficient to modulate tumor growth or metastasis in an animal. One of ordinary skill in the art can readily determine an effective amount of a compound of the present invention to be administered to an animal, for example, using routine techniques. Exemplary dosage amounts for an adult human are from about 0.05 to about 1000 mg/kg of body weight of active compound per day, which can be administered in a single dose (for example, as a bolus or as an infusion over time at or below the maximum tolerated dose) or in the form of individual divided doses (for example, as consecutive dosages below the maximum tolerated dose), such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

As used herein the term "animal" preferably includes subjects such as domestic animals, and most preferably, humans.

As used herein the term "prodrug" refers to a precursor compound that will undergo metabolic activation in vivo to produce the active drug. Thus, for example, a compound of the invention administered to a subject will undergo metabolic activation and regenerate combretastatin A-4 due to the dissociation of a compound of the present invention, for example, by the action of endogenous non-specific phosphatases in plasma.

As used herein, the term "organic amine" refers to an organic (i.e., carbon-containing) compound containing at least one primary (i.e., —NH₂), secondary (i.e., —NH—) or tertiary (i.e.,

amine group capable of forming a phosphate salt in the compound of the formula I of the present invention. Where there is more than one primary, secondary and/or tertiary amine group within said organic amine, any such group capable of doing so can form the quaternary ammonium group QH⁺ of formula I. The present definition of "organic amine" does not encompass amino acid compounds (see the provisional application entitled "Combretastatin A-4 Phosphate Mono- and Di-Amino Acid Salt Prodrugs", filed by Venit as U.S. Application Ser. No. 60/232,568 on Sep. 14, 2000, incorporated herein by reference in its entirety) nor certain compounds as described in WO 99/35150 (glucosamine, piperazine, piperidine, 6'-methoxy-cinchonan-9-ol, cinchonan-9-ol, pyrazole, pyridine, tetracycline, imidazole, adenosine, verapamil, morpholine), incorporated herein by reference in its entirety. The organic amine employed is preferably a physiologically tolerable compound selected from the following groups:

(a) organic amines having a $pK_\alpha$ greater than or equal to 7, more preferably a $pK_\alpha$ greater than or equal to 8;

(b) organic amines wherein the nitrogen forming the quaternary ammonium cation QH⁺ in the formula I is bonded to an optionally substituted aliphatic group or to an optionally substituted heterocyclic non-aromatic group (or two or three such optionally substituted aliphatic and/or heterocyclic non-aromatic groups in the case of secondary or tertiary amines, respectively). The "aliphatic group" is a straight or branched-chain, saturated or unsaturated hydrocarbon (e.g., alkane, alkene or alkyne) having from 1 to 20, preferably 1 to 12, more preferably 1 to 6 carbon atoms in the chain. The "heterocyclic non-aromatic group" is a saturated or partially unsaturated ring containing the nitrogen forming the quaternary ammonium cation QH⁺ in the formula I as well as, optionally, other heteroatoms in the ring such as O, S or additional N atoms. "Optional substituents" are preferably one or more substituents providing an organic amine which, when employed in the formula I of the present invention, results in phosphate salts of the formula I which are crystalline and practically nonhygroscopic or nonhygroscopic. Preferred "optional substituents" include hydroxyl, amino (i.e., —NH₂), or alkoxy (i.e., —O-alkyl) groups, most preferably, one or more hydroxyl groups; and/or (c) organic amines wherein the nitrogen forming the quaternary ammonium cation QH⁺ in the formula I is a primary amine bonded to an optionally substituted aliphatic group or a secondary amine bonded to two optionally substituted aliphatic groups, wherein the preferred optional substituents are one or more hydroxyl or amino groups, most preferably, hydroxyl groups.

Of course, any given organic amine selected as a preferred amine for use in the present invention may have the properties of two or more groups (a) to (c) described above (for example, have a $pK_a$ greater than or equal to 7 and be an optionally substituted aliphatic amine as described in (c)).

Any organic amine so defined is suitable for use in the compounds of formula I of the present invention, as well as the present pharmaceutical compositions and methods. The term "organic amine" includes compounds in salt form with other acidic and/or basic moieties (where, for example, one amine group forms the phosphate salt of formula I and another amine group forms a salt with an acidic moiety). Thus, the remainder of the organic amine comprised within a compound of the present invention can also contain salt moieties.

Exemplary organic amines include, but are certainly not limited to, tromethamine, diethanolamine, glucamine, N-methylglucamine, ethylenediamine, and 2-(4-imidazolyl) ethyl amine.

A combretastatin A-4 phosphate "mono-organic amine" salt of the formula I contains one organic amine group Q as part of R¹ or R² as defined above; a combretastatin A-4 phosphate "di-organic amine" salt of the formula I contains two organic amine groups Q, one part of R¹ and one part of R² as defined above. "Mono-organic amine" salts of the formula I are preferred. Corresponding definitions apply for "mono-amino acid", "di-amino acid", "mono-amino acid ester" and "di-amino acid ester".

Any suitable amino acid has applications herein, including numerous natural and non-natural amino acids having applications in a compound of the present invention. Particular examples include, but certainly are not limited to ornithine, histidine, lysine, arginine, and tryptophan, to name only a few.

As used herein, the term "amino acid" refers to a compound containing a basic amino group (NH₂) and an acidic carboxylic acid group (COOH), including such compounds in zwitterionic form (where the amino and carboxyl groups together form a zwitterion or internal salt), or in salt form with other acidic and/or basic moieties (where, for example, the amino acid contains a carboxylic acid group in addition to the α-COOH group, and the former is in salt form with an alkali metal). Thus, the remainder of an amino acid comprised within a compound of the present invention can also contain salt moieties. The term includes non-natural as well as natural amino acids, such as α-amino acids (especially L-amino acids) many of which are the building blocks of proteins. The term "natural amino acids" refers to the 20 amino acids that are common in all proteins, i.e., glycine, alanine, valine, leucine, isoleucine, proline, serine, threonine, cysteine, methionine, asparagine, glutamine, phenylalanine, tyrosine, tryptophan, lysine, arginine, histidine, aspartate, and glutamate. The phrase "non-natural amino acids" refers to amino acids that are generally not common in all proteins, such as 4-hydroxyproline, 5-hydroxylysine, N-methyllysine, γ-carboxyglutamate, selenocystein, ornithine and citrulline. Amino acids having two or more nitrogen atoms are suitable for use in the compounds of formula I of the present invention when Q has definition (B), as well as the present pharmaceutical compositions and methods.

As used herein, the phrase "side chain" with respect to an amino acid is that moiety of an amino acid which is different for each amino acid, especially the group bonded to the carbon linking the —NH₂ and —COOH groups of an amino acid.

As used herein, the term "practically nonhygroscopic", in reference to a compound, preferably denotes less than 1% water weight gain per weight of compound (more preferably, less than 0.5% water weight gain per weight of compound) measured under the following conditions: a temperature of approximately 25° C., relative humidities of from 20% to 95%, and at equilibrium conditions (i.e., measured at a time wherein the rates of moisture sorption and desorption have equilibrated), relative to measurement under 25° C. and 0% relative humidity conditions. As used herein, the term "nonhygroscopic", in reference to a compound, preferably denotes no measurable weight gain per weight of compound as measured above.

As used herein in reference to an amino acid, the term "ester" refers to a carboxylic acid group (i.e., a group —COOH) of the amino acid which is in the form —COO(G) where G is an organic moiety such as an unsubstituted or substituted alkyl, alkenyl, alkynyl, cycloalkyl, cycloalkenyl, aryl or heterocyclo group. Preferred as groups G are $C_{1-6}$ alkyl groups such as methyl or ethyl. Most preferred as amino acid esters are $C_{1-6}$ alkyl esters of glycine, such as glycine methyl ester or glycine ethyl ester.

As used herein, the term "salt" refers to a compound of the present invention which is an ionic compound, for example, having an ionic bond between the quaternary nitrogen of the organic amine, amino acid or amino acid ester moiety $QH^+$ and the phosphate moiety of combretastatin A4 phosphate.

As used herein, an "ionic bond" is a chemical bond that forms by the electrostatic attraction between positive and negative ions or chemical structures. Such a bond can be readily dissociated (or ionized) in an aqueous solution. Dissolution of a compound of the present invention in a solvent, particularly an aqueous solvent, as well as the lyophilization of such a solution are embodiments encompassed by the present invention.

As used herein, the phrase "physiologically tolerable" in describing a chemical specie present in vivo, such an organic amine, amino acid or amino acid ester, refers to the inability of the chemical specie to induce side effects unacceptable under the conditions of treating the animal. Preferably, "physiologically tolerable" chemical species produce no deleterious side effects.

As explained above, the present invention is directed towards a method for modulating the growth or metastasis of tumors, preferably solid tumors, using a compound of the present invention. As used herein, the terms "tumor" or "tumor growth" can be used interchangeably, and refer to an abnormal growth of tissue resulting from uncontrolled progressive multiplication of cells and serving no physiological function. A solid tumor can be malignant, e.g. tending to metastasize and being life threatening, or benign. Examples of solid tumors that can be treated according to a method of the present invention include sarcomas and carcinomas such as, but not limited to: fibrosarcoma, myxosarcoma, liposarcoma, chondrosarcoma, lymphoma, such as non-Hodgkin's lymphoma, osteogenic sarcoma, chordoma, esophageal tumors, angiosarcoma, osteosarcoma, endotheliosarcoma, lymphangiosarcoma, lymphangioendotheliosarcoma, synovioma, synovial sarcoma, mesothelioma, Ewing's tumor, leiomyosarcoma, rhabdomyosarcoma, colon carcinoma, colorectal cancer, gastric cancer, pancreatic cancer, breast cancer such as metastatic breast cancer, ovarian cancer, prostate cancer, squamous cell carcinoma, basal cell carcinoma, adenocarcinoma, adenocarcinoma of the colon and rectum, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, medullary thyroid tumor, Wilms' tumor, cervical cancer, testicular tumor, lung tumors such as non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Moreover, tumors comprising dysproliferative changes (such as metaplasias and dysplasias) can be treated or prevented with a compound or method of the present invention in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W.B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, *Medicine*, 2d Ed., J. B. Lippincott co., Philadelphia.

Other examples of tumors that are benign and can be treated with a compound or method of the present invention include arteriovenous (AV) malformations, particularly in intracranial sites and myoleomas.

The compounds of the present invention are also useful in methods for the treatment of non-malignant vascular proliferative disorders such as macular degeneration, psoriasis and restenosis, and, in general, in the treatment of inflammatory diseases characterized by vascular proliferation. Such diseases and disorders are described in WO 00/48606, incorporated herein by reference in its entirety.

Pharmaceutical Compositions

The present invention also extends to a pharmaceutical composition comprising a compound of the present invention as described above, and a pharmaceutically acceptable carrier thereof. The phrase "pharmaceutically acceptable" refers to molecular entities and compositions that are physiologically tolerable and preferably do not typically produce an allergic or similar untoward reaction, such as gastric upset, dizziness and the like, when administered to a human. Preferably, as used herein, the term "pharmaceutically acceptable" means approved by a regulatory agency of the Federal or a State government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil sesame oil, alcohols, e.g., ethanol propanol, polyethylene glycol, propylene glycol sorbitol, glycerine, etc., Cremophor and the like, including mixtures thereof. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A pharmaceutical composition of the present invention can be for administration for injection, or for oral, pulmonary, nasal, transdermal, ocular or other forms of administration. In general comprehended by the invention are pharmaceutical compositions comprising effective amounts of a compound of the present invention together with, for example, pharmaceutically acceptable diluents, preservatives, solubilizers, emulsifiers, adjuvants and/or other carriers. Such compositions include diluents of various buffer content (e.g., TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate), pH and ionic strength; additives such as detergents and solubilizing agents (e.g., surfactants such as Pluronics, Tween 20, Tween 80 (Polysorbate 80), Cremophor, polyols such as polyethylene glycol, propylene glycol, etc.), anti-oxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes. Hyaluronic acid may also be used Such compositions can be employed to influence the physical state, stability, rate of in vivo release, and rate of in vivo clearance of a compound of the present invention. See, e.g., Remington's Pharmaceutical Sciences, 18th Ed (1990, Mack Publishing Co., Easton, Pa. 18042) pages 1435-1712 which are herein incorporated by reference. The compositions can, for example, be prepared in liquid form, or can be in dried powder, such as lyophilized form. Particular methods of administering such compositions are described infra.

pH adjustment can be employed as desired. It is preferred—for example, to enhance the solubility of compounds of the present invention—to adjust the pH of pharmaceutical compositions comprising these compounds to a pH greater than 7, more preferably, to a pH greater than 8 (such as to a pH of about 8.5).

For CA4P prodrug salts such as those of formula I of the present invention, active parent (CA4) formation occurs at lower pH. The present inventors have found that addition of a buffer/pH adjustment agent prevents pH drop during freezing thus providing a more stable lyophile formulation. It has further been surprisingly found that, for lyophile formulations of CA4P prodrug salts such as those of the formula I of the present invention, pH adjustment employing sodium hydroxide as the pH adjustment agent can result in the formation of the active parent (cis) CA4 (which is minimally soluble in water and can form undesirable particulates in an aqueous solution), and that use of a pH adjustment agent other than sodium hydroxide can mitigate CA4 formation. Use of TRIS as a pH adjustment agent and buffer, for example, mitigates the formation of the active parent (cis) CA4 relative to the use of sodium hydroxide for pH adjustment, and thus is particularly preferred for use in compositions of the present invention. For example, observations have been made for compounds of the formula I where Q is either TRIS or histidine such that lyophiles prepared using NaOH as a pH adjustment agent showed hydrolysis to parent cis-CA4 upon storage whereas pH adjustment using a suitable buffering agent other than NaOH, for example, TRIS mitigated formation of the insoluble parent. Another aspect of the present invention therefore relates to pharmaceutical lyophile compositions (preferably prepared from pH-adjusted solutions), comprising a compound of the present invention and a pH adjustment agent other than sodium hydroxide, preferably, comprising an organic base such as an amino acid or organic amine, especially TRIS, as the pH adjustment agent. Thus, while use of sodium hydroxide is encompassed within lyophile compositions of the present invention, such use is less preferred, for example, for pharmaceutical compositions to be administered intravenously where solids formation is undesirable.

Pharmaceutical compositions, for example, solutions (especially aqueous solutions, for example, at concentrations at 15 mg/mL, 30 mg/mL and 60 mg/mL) can also be prepared comprising a compound of the present invention and a pH adjustment agent including sodium hydroxide, preferably, comprising an organic base such as an amino acid such as arginine, glycine, or organic amine, e.g. ethanolamine, especially TRIS, as the pH adjustment agent. The aqueous solution stability increases as the pH of the formulation increases from pH 9.0 to pH 10.5. The solution stability is also better at higher ionic strengths. For example, a solution formulation with NaOH as a pH adjusting agent at pH 10 can indicate comparable stability to the lyophilized formulation prepared with TRIS as a buffering agent at pH 8.5.

Protection from light is preferably employed for the pharmaceutical compositions of the present invention.

Methods for Modulating Tumor Growth or Metastasis

Combretastatin A-4 is a very potent antimitotic agent derived from the stem wood of *Combretum caffrum*, and shows potent toxicity against a wide variety of human cancer cell lines. Consequently, administering a compound or pharmaceutical composition of the present invention to a subject can reduce tumor growth and/or metastasis in the subject or alternatively, if the subject has no detectable metastasis or tumor growth, will prevent metastasis and/or tumor growth. Naturally, a compound of the present invention can be administered alone or with a pharmaceutically acceptable carrier.

Hence, the present invention is directed towards methods for modulating tumor growth or metastasis comprising, inter alia, the administration of an effective amount of a mono- or di-organic amine combretastatin A-4 phosphate prodrug salt of the present invention that rapidly regenerates combretastatin A-4 in vivo. As explained above, the phrase "effective amount" as used herein refers to the amount of compound of the present invention administered to a subject that is sufficient to modulate tumor growth or metastasis, such as to decrease tumor growth and metastasis in an animal or alternatively to prevent formation of tumor growth in an animal that lacked any tumor formation prior to administration. One of ordinary skill in the art can readily determine the effective amount of a compound of the present invention to administer, for example, using routine techniques.

Moreover, numerous means for administrating a compound of the present invention have applications in a method of the present invention. In particular, a compound or pharmaceutical composition of the present invention can be introduced parenterally, transmucosally, e.g., orally, nasally, or rectally, or transdermally. Preferably, administration is parenteral, e.g., via intravenous injection, and also including, but not limited to, intra-arteriole, intramuscular, intradermal, subcutaneous, intraperitoneal, intraventricular, and intracranial administration. The compound or pharmaceutical composition can, for example, be introduced by injection into the tumor(s) being treated or into tissues surrounding the tumor(s). "Mucosal penetration enhancer" refers to a reagent that increases the rate or facility of transmucosal penetration of a compound of the present invention, such as but not limited to, a bile salt, fatty acid, surfactant or alcohol. In specific embodiments, the permeation enhancer can be sodium cholate, sodium dodecyl sulfate, sodium deoxycholate, taurodeoxycholate, sodium glycocholate, dimethylsulfoxide or ethanol. Suitable penetration enhancers also include glycyrrhetinic acid (U.S. Pat. No. 5,112,804 to Kowarski) and polysorbate-80, the latter preferably in combination with a non-ionic surfactant such as nonoxynol-9, laureth-9, poloxamer-124, octoxynol-9, or lauramide-DEA (European Patent EP 0 242 643 B1 by Stoltz).

In another embodiment, according to a method of the present invention, a compound or pharmaceutical composition of the present invention can be delivered in a vesicle, in particular a liposome [see Langer, *Science* 249:1527-1533 (1990); Treat et al., in *Liposomes in the Therapy of Infectious Disease and Cancer*, Lopez-Berestein and Fidler (eds.), Liss: New York, pp. 353-365 (1989); Lopez-Berestein, ibid., pp. 317-327; see generally ibid.].

In yet another embodiment, such a compound or pharmaceutical composition can be delivered in a controlled release system, such as using an intravenous infusion, an implantable osmotic pump, a transdermal patch, liposomes, or other modes of administration. In a particular embodiment, a pump may be used [see Langer, supra; Sefton, *CRC Crit. Ref. Biomed Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of the target tissues of the subject, thus requiring only a fraction of the systemic dose [see, e.g., Goodson, in *Medical Applications of Controlled Release*, supra, vol. 2, pp. 115-138 (1984)]. Preferably, a controlled release device is introduced into an animal in proximity of the site of inappropriate immune activation or a tumor. Other controlled release systems are discussed in the review by Langer [*Science* 249: 1527-1533 (1990)].

Parenteral Administration

As explained above, a compound or pharmaceutical composition of the present invention can be administered parenterally to a subject, and thus avoid administration via a subject's gastrointestinal tract. Particular parenteral administration techniques having applications herein include, but certainly are not limited to intravenous (bolus or infusion) injections, intraperitoneal injections, subcutaneous injections, intramuscular injections, or catheterizations, to name only a few. Exemplary compositions for parenteral administration include injectable solutions or suspensions which can contain, for example, suitable non-toxic, parenterally acceptable diluents or solvents, such as mannitol, 1,3-butanediol, water, buffered aqueous systems, Ringer's solution, an isotonic sodium chloride solution, or other suitable dispersing or wetting and suspending agents, including synthetic mono- or diglycerides, and fatty acids, including oleic acid, alcohols, and/or Cremophor. pH adjustment can be employed as desired.

Nasal Delivery

Nasal or transmucosal delivery of a compound or pharmaceutical composition of the present invention is also contemplated. Nasal delivery allows the passage of such a compound to the blood steam directly after administering an effective amount of the compound to the nose, without the necessity for deposition of the product in the lung. Formulations for nasal delivery include those with dextran or cyclodextrin, as well as other polymers such as polyvinylpyrrolidones, methyl cellulose or other celluloses.

For nasal administration, a useful device is a small hard bottle to which a metered dose sprayer is attached. In one embodiment, the metered dose is delivered by drawing a compound or pharmaceutical composition of the present invention into a chamber of defined volume, which has an aperture dimensioned to aerosolize an aerosol formulation by forming a spray when a liquid in the chamber is compressed. The chamber is compressed to administer the compound or pharmaceutical composition. In a specific embodiment, the chamber is a piston arrangement. Such devices are commercially available.

Alternatively, a plastic squeeze bottle having an aperture or opening dimensioned to aerosolize an aerosol formulation can be used. Aerolsolization occurs when the bottle is squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of a compound or pharmaceutical composition of the present invention.

For transmucosal delivery, use of permeation enhancers is also contemplated.

Pulmonary Delivery

Also contemplated herein is pulmonary delivery of a compound or pharmaceutical composition of the present invention. A compound or pharmaceutical composition of the present invention can be delivered to the lungs of a mammal while inhaling and traverses across the lung epithelial Lining to the blood stream. Other reports of this include Adjei et al. [*Pharmaceutical Research*, 7:565-569 (1990); Adjei et al., *International Journal of Pharmaceutics*, 63:135-144 (1990) (leuprolide acetate); Braquet et al., *Journal of Cardiovascular Pharmacology*, 13(suppl. 5):143-146 (1989) (endothelin-1); Hubbard et al., *Annals of Internal Medicine*, Vol. III, pp. 206-212 (1989) ($\alpha$1-antitrypsin); Smith et al., *J. Clin. Invest.* 84: 1145-1146 (1989) ($\alpha$-1-proteinase); Oswein et al., "Aerosolization of Proteins", *Proceedings of Symposium on Respiratory Drug Delivery II*, Keystone, Colo., March, (1990) (recombinant human growth hormone); Debs et al., *J. Immunol.* 140:3482-3488 (1988) (interferon-$\gamma$ and tumor necrosis factor alpha), Platz et al., U.S. Pat. No. 5,284,656 (granulocyte colony stimulating factor)]. A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of pharmaceutical composition of the present invention. Typically, each formulation is specific to the type of device employed and may involve the use of an appropriate propellant material, in addition to the usual diluents, adjuvants and/or other carriers useful in therapy. Also, the use of liposomes, microcapsules or microspheres, inclusion complexes, or other types of carriers is contemplated. Chemically modified pharmaceutical composition of the present invention may also be prepared in different formulations depending on the type of chemical modification or the type of device employed.

Formulations suitable for use with a nebulizer, either jet or ultrasonic, will typically comprise a compound or pharmaceutical composition of the present invention dissolved in water at a concentration of about 0.1 to 25 mg of biologically active ingredients per mL of solution. The formulation may also include a buffer and a simple sugar (e.g., for stabilization and regulation of osmotic pressure of a pharmaceutical composition of the present invention). The nebulizer formulation may also contain a surfactant, to reduce or prevent surface induced aggregation of a compound or pharmaceutical composition of the present invention caused by atomization of the solution in forming the aerosol.

Formulations for use with a metered-dose inhaler device will generally, for example, comprise a finely divided powder containing a compound or pharmaceutical composition of the present invention suspended in a propellant with the aid of a surfactant. The propellant may be any suitable material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

The liquid aerosol formulations contain a compound or pharmaceutical composition of the present invention and a dispersing agent in a physiologically acceptable diluent. The dry powder aerosol formulations of the present invention can contain a finely divided solid form of a compound or pharmaceutical composition of the present invention and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations include the construction of the delivery device, additional components in the formulation, and particle characteristics. These aspects of nasal or pulmonary administration of a drug are well known in the art, and manipulation of formulations, aerosolization means and construction of a delivery device can be readily achieved by one of ordinary skill in the art.

In a particular embodiment, the mass median dynamic diameter will be 5 micrometers or less in order to ensure that the drug particles reach the lung alveoli (Wearley, L. L., 1991, 1991, Crit. Rev. in Ther. Drug Carrier Systems 8:333).

As noted above, in a particular aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Often, the aerosolization of a liquid or a dry powder formulation for inhalation into the lung will require a propellant. The propellant may be any propellant generally used in the art. Specific nonlimiting examples of such useful propellants are a chloroflourocarbon, a hydrofluorocarbon, a hydrochlorofluorocarbon, or a hydrocarbon, including triflouromethane, dichlorodiflouromethane, dichlorotetrafluoroethanol, and 1,1,1,2-tetraflouroethane, or combinations thereof.

Systems of aerosol delivery, such as the pressurized metered dose inhaler and the dry powder inhaler are disclosed in Newman, S. P., *Aerosols and the Lung*, Clarke, S. W. and Davia, D. editors, pp. 197-22 and can be used in connection with the present invention.

Liquid Aerosol Formulations

The present invention provides for liquid aerosol formulations and dosage forms of a compound or pharmaceutical composition of the present invention. In general, such dosage forms contain a compound or pharmaceutical composition of the present invention in a pharmaceutically acceptable diluent. Pharmaceutically acceptable diluents include, but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0-8.0 range, or water.

The liquid aerosol formulation of the present invention may include, as optional ingredients, pharmaceutically acceptable carriers, diluents, solubilizing or emulsifying agents, surfactants and excipients.

The formulations of the present embodiment may also include other agents useful for pH maintenance, solution stabilization, or for the regulation of osmotic pressure. Examples of the agents include, but are not limited to salts, such as sodium chloride, or potassium chloride, and carbohydrates, such as glucose, galactose or mannose, and the like.

Aerosol Dry Powder Formulations

It is also contemplated that the present aerosol formulation can be prepared as a dry powder formulation comprising a finely divided powder form of a compound or pharmaceutical composition of the present invention and a dispersant.

Formulations for dispensing from a powder inhaler device can comprise a finely divided dry powder containing a compound or pharmaceutical composition of the present invention, and may also include a bulking agent, such as lactose, sorbitol sucrose, or mannitol in amounts which facilitate dispersal of the powder from the device, e.g., 50 to 90% by weight of the formulation. A compound or pharmaceutical composition of the present invention should most advantageously be prepared in particulate form with an average particle size of less than 10 microns, most preferably 0.5 to 5 microns, for most effective delivery to the distal lung.

In another embodiment, the dry powder formulation can comprise a finely divided dry powder containing a compound or pharmaceutical composition of the present invention, a dispersing agent and also a bulking agent. Bulking agents useful in conjunction with the present formulation include such agents as lactose, sorbitol, sucrose, or mannitol, in amounts that facilitate the dispersal of the powder from the device.

Transdermal Administration

Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1994 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Moreover, a compound or pharmaceutical composition of the present invention can be administered topically. For example, a compound can be mixed with a salve carrier forming a composition that can be rubbed onto the skin. Alternatively, a compound of the present invention can be dissolved into a solvent that is well known to permeate the skin. A particular example of such a solvent is dimethyl sulfoxide (DMSO). Gel formulations are also contemplated.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include, for example, tablets, capsules, pills, troches or lozenges, cachets or pellets. Also, liposomal or proteinoid encapsulation may be used to formulate a compound or pharmaceutical composition of the present invention (as, for example, proteinoid microspheres reported in U.S. Pat. No. 4,925,673). Liposomal encapsulation can be used and the liposomes can be derivatized with various polymers (e.g., U.S. Pat. No. 5,013,556). A description of possible solid dosage forms for therapeutic use is given by Marshall K. In: *Modern Pharmaceutics* Edited by G. S. Banker and C. T. Rhodes Chapter 10, 1979, herein incorporated by reference. The formulation can include a compound or pharmaceutical composition of the present invention and inert ingredients which allow for protection against the stomach environment, and release of the biologically active material in the intestine.

Also specifically contemplated are oral dosage forms of a compound of the present invention, wherein the compound may be chemically modified so that oral delivery of the derivative is efficacious. Generally, the chemical modification contemplated is the attachment of at least one moiety to the component molecule itself; where the moiety permits (a) inhibition of proteolysis; and (b) uptake into the blood stream from the stomach or intestine. Also desired is the increase in overall stability of a compound of the present invention and increase in circulation time in the body. Examples of such moieties include: polyethylene glycol, copolymers of ethylene glycol and propylene glycol, carboxymethyl cellulose, dextran polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For a compound of the present invention, the location of release may be the stomach, the small intestine (the duodenum, the jejunum, or the ileum), or the large intestine. One skilled in the art can prepare formulations which will not dissolve in the stomach, yet will release a compound of the present invention in the duodenum or elsewhere in the intestine. Preferably, the release will avoid the deleterious effects of the stomach environment, either by protection of the compound or by release of the biologically active material beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

A compound of the present invention can, for example, be included in the formulation as fine multi-particulates in the form of granules or pellets of particle size about 1 mm. The formulation of the material for capsule administration could also be as a powder, lightly compressed plugs or even as tablets. Also, a compound or pharmaceutical composition of the present invention can be prepared by compression.

Colorants and flavoring agents may all be included. For example, the compound can be formulated (such as by liposome or microsphere encapsulation) and then further contained within an edible product, such as a refrigerated beverage containing colorants and flavoring agents.

One may dilute or increase the volume of a compound of the present invention or a pharmaceutical composition with an inert material. These diluents could include carbohydrates, especially mannitol a-lactose, anhydrous lactose, cellulose, sucrose, modified dextrans and starch. Certain inorganic salts may be also used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of a pharmaceutical composition of the present invention into a solid dosage form. Materials used as disintegrates include, but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold a compound or pharmaceutical composition of the present invention together to form a hard tablet and include materials from natural products such as acacia, tragacanth, starch and gelatin Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of a pharmaceutical composition of the present invention to prevent sticking during the formulation process. Lubricants may be used as a layer between the therapeutic and the die wall, and these can include, but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of a compound of the present invention during formulation and to aid rearrangement during compression can be added. The glidants may include starch, talc, pyrogenic silica and hydrated silicoaluminate.

Additives which potentially enhance uptake of a compound of the present invention administered orally are, for instance, the fatty acids oleic acid, linoleic acid and linolenic acid.

Controlled release oral formulation may be desirable. The drug could be incorporated into an inert matrix which permits release by either diffusion or leaching mechanisms, e.g., gums. Slowly degenerating matrices may also be incorporated into the formulation. Some enteric coatings also have a delayed release effect.

Another form of a controlled release of a compound of the present invention is by a method based on the Oros therapeutic system (Alza Corp.), i.e. the drug is enclosed in a semipermeable membrane which allows water to enter and push drug out through a single small due to osmotic effects.

Other coatings may be used for the formulation. These include a variety of sugars which could be applied in a coating pan. A compound of the present invention could also be given in a film coated tablet and the materials used in this instance can be, for example, divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group includes the enteric materials that are commonly esters of phthalic acid A mix of materials might be used to provide the optimum film coating. Film coating may be carried out in a pan-coater or in a fluidized bed or by compression coating.

Methods for Preparation

Compounds of the formula I described above can be prepared by any suitable method, for example, by contacting the desired compound Q (especially, organic amine, amino acid or amino acid ester) with the free acid of combretastatin A-4 phosphate ("CA4P free acid") which has the structure:

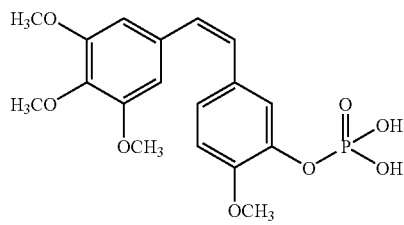

in relative amounts sufficient to obtain a mono- or di-organic amine salt, mono- or di-amino acid salt or mono- or di-amino acid ester salt of formula I of the present invention (e.g., 1:1 molar ratio to obtain a 1:1 mono-organic amine salt or mono-amino acid salt, or a molar excess of organic amine in an appropriate solvent (e.g., a solvent selected for a desirable pKa) to obtain a di-organic amine salt). CA4P free acid can be obtained from CA4P disodium salt, for example, as described in the Examples infra. The compound Q, such as organic amine or amino acid, and CA4P free acid can, for example, be contacted in a suitable solvent (preferably, a $C_1$-$C_6$ alcohol such as isopropanol or aqueous mixtures thereof), preferably followed by collection of the compound of formula I as a crystalline compound by means such as filtration. The term "solvent" includes a single solvent, or mixtures of two or more solvents forming miscible or biphasic solvent mixtures. Where desired, the compound Q can be added in the form of a salt, preferably a pharmaceutically acceptable salt, as described in the Examples infra.

Thus, the present invention extends to a process for preparing a compound having a general structure of the formula I:

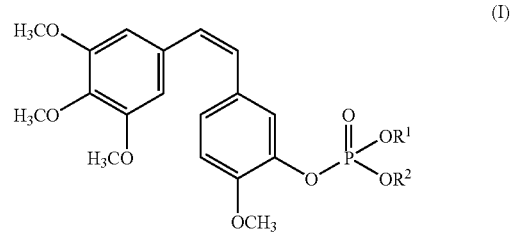

where one of —$OR^1$ or —$OR^2$ is —O—$QH^+$, and the other is hydroxyl or —O—$QH^+$, and Q is (A) an organic amine containing at least one nitrogen which, together with a proton, forms a quaternary cation $QH^+$;

(B) an amino acid containing at least two nitrogen atoms where one of the nitrogen atoms, together with a proton, forms a quaternary ammonium cation $QH^+$; or (C) an amino acid containing one or more nitrogen atoms where one of the nitrogen atoms, together with a proton, forms a quaternary ammonium cation QH+ and where, further, all carboxylic acid groups of the amino acid are in the form of esters.

Such a method of the present invention comprises the step of contacting, in a solvent, CA4P free acid having the structure:

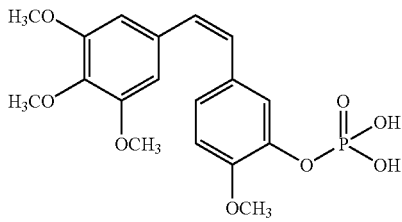

with a compound Q, where Q is (A) an organic amine containing at least one nitrogen atom which is capable of forming, together with a proton, a quaternary ammonium cation QH+;

(B) an amino acid containing at least two nitrogen atoms where one of the nitrogen atoms, together with a proton, forms a quaternary ammonium cation QH+; or (C) an amino acid containing one or more nitrogen atoms where one of the nitrogen atoms, together with a proton, forms a quaternary ammonium cation QH+ and where, further, all carboxylic acid groups of the amino acid are in the form of esters.

Optionally, a compound of the present invention produced with a process described herein can be precipitated in crystalline form from the solvent.

In addition, the present invention extends to a process for preparing a compound having a general structure of the formula I:

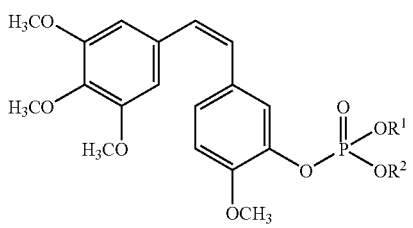

as described above, comprising the steps of contacting the CA4P free acid with a preferred compound Q (such as histidine, a glycine $C_{1-6}$ alkyl ester or, most preferably, tromethamine) in the solvent, and then collecting the resulting CA4P histidine, glycine $C_{1-6}$ alkyl ester or most preferably, tromethamine salt in crystalline form from the solvent. Naturally, as explained above, numerous solvents have applications in a process of the present invention. Particular examples, include, but certainly are not limited to $C_1$-$C_6$ alcohols, such as isopropanol or aqueous mixtures thereof. In a preferred embodiment of the present invention, a process described herein produces the compound CA4 P mono-tromethamine ("mono-TRIS salt of CA4P" or "CA4P mono TRIS salt"). In another preferred embodiment of the present invention a process described herein produces the compound CA4P mono-L-histidine.

Mixtures of a compound Q (organic amine, amino acid or amino acid ester) and CA4P free acid, preferably in a solution such as an aqueous solution, are also contemplated herein as embodiments of the invention. Thus, the present invention further provides compositions formed by mixing compounds comprising:

(a) CA4P free acid having the structure of:

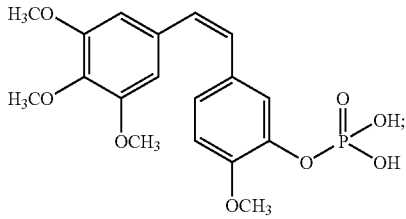

(b) a compound Q, wherein Q is (A) an organic amine containing at least one nitrogen atom which is capable of forming, together with a proton, a quaternary ammonium cation QH+;

(B) an amino acid containing at least two nitrogen atoms where one of the nitrogen atoms, together with a proton, forms a quaternary ammonium cation QH+; or (C) an amino acid containing one or more nitrogen atoms where one of the nitrogen atoms, together with a proton, forms a quaternary ammonium cation QH+ and where, further, all carboxylic acid groups of the amino acid are in the form of esters.

Optionally, a composition of the present invention can further comprise a pharmaceutically acceptable carrier.

The present invention may be better understood by reference to the following non-limiting Examples, which are provided as exemplary of the invention. The following Examples are presented in order to more fully illustrate the preferred embodiments of the invention. They should in no way be construed, however, as limiting the broad scope of the invention.

Example 1

CA4P Prodrug Mono-Tromethamine Salt

In an embodiment of the present invention, a CA4P mono-tromethanine salt is described as a non-limiting example of a compound of the present invention. With the information described herein, one of ordinary skill in the art can readily produce a variety of CA4P prodrug mono- or di-organic amine salts, such as by addition of the desired organic amine to CA4P free acid by a procedure analogous to that described following, all of which are encompassed by the present invention and the appended claims.

Reagents and Methods

All reagents and chemicals were obtained from commercial sources and used without further purification: Tris(hydroxymethyl)aminomethane (TRIS) (Aldrich Chemical Co. 99.9+% labeled, Lot #01404PU), isopropyl alcohol (B&J Brand, High purity solvent grade). Multi-nuclei NMR spectra were recorded on Bruker DRX 400 spectrometer. The $^1$H and $^{13}$C NMR chemical shifts are reported in ppm relative to tetramethylsilane. (The $^{13}$C NMR chemical shifts were determined using methanol ("MeOH") as external standard). The $^{13}$C NMR spectra were acquired with proton decoupled {$^{1}$H}. The 2D NMR experiments (HMQC (Heteronuclear Multiple Quantum Correlation spectroscopy, an inverse chemical shift correlation experiment to determine which $^{1}$H's of the molecule are bonded to which $^{13}$C nuclei (or other X nuclei)); and HMQC (Heteronuclear Multiple Bond Correlation spectroscopy, a modified version of HMQC suitable to determine long-range $^{1}$H-$^{13}$C connectivity, as well as the structure and $^{1}$H and $^{13}$C assignments of the molecule)) were conducted to aid the assignments of the $^{1}$H and $^{13}$C NMR signals to the structure. "CA4P disodium salt" is the compound having the following structure:

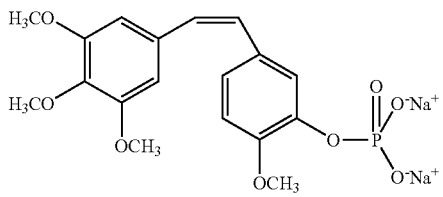

(See U.S. Pat. No. 5,561,122 mentioned above).

CA4P Mono-Tromethamine Salt

Aqueous IPA TRIS solution (0.19 M). A 0.19 M TRIS solution was prepared by dissolving 1.61 g of TRIS (13.3 mmol) in 7 mL of deionized water, and added 63 mL of isopropyl alcohol ("IPA") to the resulting aqueous solution (10% water in IPA).

CA4P free acid stock solution in isopropyl alcohol (0.19M). CA4P disodium salt (12.15 g, 27.6 mmol) was dissolved in 70 mL of deionized water. Ethyl acetate (250 mL) and a saturated aqueous sodium chloride solution (150 mL) were added to the resulting solution with rapid stirring. A white cake was formed. A solution of 0.5 N hydrochloric acid (325 mL) was added portion-wise to dissolve the cake (the final pH of the aqueous phase was ca. 1 (pH paper)). The organic phase was separated. The aqueous phase was extracted with ethyl acetate (3×200 mL). The organic phases were combined and dried over anhydrous Na$_2$SO$_4$. Filtration and solvent evaporation (Rotavapor, water bath temperature=40° C.) yielded a thick film of CA4P free acid which was dissolved in 100 mL of IPA. The concentration of the resulting solution was determined to be 0.19 M by $^{1}$H NMR, using the following titration method: pipetted 45 µL of L-histidine solution (0.17 M) and 30 µL of CA4P free acid solution into a 4-mL HPLC vial. The solvents were evaporated to dryness using the Rotavapor. The solid was dissolved in 0.7 mL of D$_2$O and analyzed by $^{1}$H NMR to give a 1:0.75 ratio of histidine to CA4P free acid. A total of 19 mmol of CA4P free acid was obtained (69% yield).

CA4P mono-TRIS salt. A 200-mL round bottom flask was charged with 70 mL of the CA4P flee acid solution prepared as above (0.19 M, 13.3 mmol). 70 mL of the aqueous IPA TRIS solution prepared as above (0.19 M, 13.3 mmol) was added portion-wise to the CA4P free acid solution with rapid stirring. The resulting white slurry was stirred at ambient temperature for 18 hours (overnight), followed by cooling to 0° C. (ice-bath) for 30 min. The crystalline solid was isolated by filtration through a Whatman #54 filter paper with suction, washed with cold isopropyl alcohol, and dried in a stream of air for 5 hours and then in vacuo (vacuum desiccator) for 113 hours to yield 7.01 g of CA4P mono-TRIS salt as a white solid. The results of the $^{1}$H NMR analysis showed that the final product contained IPA (ca. 0.9 wt %) as a residual solvent (13.4 mmol, quantitative yield). The CA4P mono-TRIS salt has the structure of formula Ia, where the olefin group bridging the phenyl moieties of the core is in the cis configuration as in the combretastatin A-4 phosphate staring material.

Characterization of CA4P mono TRIS Salt

NMR and Elemental Analysis $^{1}$H NMR (400 MHz, D$_2$O) δ 3.52 (s, 6H, C(15)H$_3$ and C(17)H$_3$), 3.56 (s, 6H, C(20)H$_2$, C(21)H$_2$, C(22)H$_2$), 3.59 (s, 3H, C(16)H$_3$), 3.67 (s, 3H, C(18)H$_3$), 6.38 (d, J=11.7 Hz, 1H, C(8)H), 6.46 (d, J=11.7 Hz, 1H, C(7)H), 6.48 (s, 2H, C(10)H and C(14)H, 6.79 (d, J=8.8 Hz, 1H, C(3)H), 6.85 (broad d, J=8.8 Hz, 1H, C(4)H), 7.06 (broad s, 1H, C(6)H); $^{13}$C NMR (100 MHz, {$^{1}$H}, D$_2$O) δ 56.9 (2C, C15, C17), 57.0 (C18), 60.3 (3C, C20, C21, C22), 62.0 (C16), 62.4 (C19), 107.5 (2C, C10, C14), 113.9 (C3), 122.6 (d, J$_{PC}$=3.1 Hz, C6), 125.9 (C4), 130.0 (C8), 130.8 (C7), 1312 (C5), 134.7 (C9), 136.8 (C12), 142.2 (d, J$_{PC}$=7.7 Hz, C1), 150.6 (d, J$_{PC}$=6.1 Hz, C2), 153.2 (2C, C11 and C13). Anal. Calcd for C$_{22}$H$_{32}$NO$_{11}$P: C, 51.06; H 6.23; N, 2.70; P, 5.98. Found. C, 51.07; H, 6.39; N, 2.58; P, 5.93.

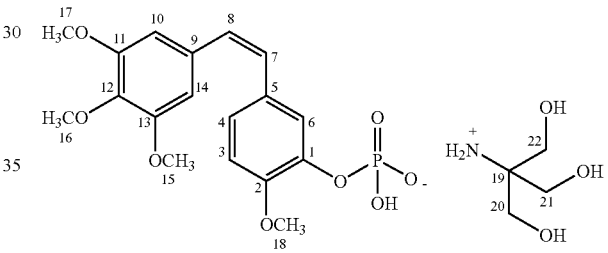

Hygroscopicity

The mono TRIS salt of CA4P of this Example was found to be practically nonhygroscopic at 25° C. under ambient and high humidity conditions. This was an unexpected result, because other salt forms of CA4P free acid are hygroscopic under similar conditions. The moisture sorption profile of the mono TRIS salt of CA4P is shown in FIG. 1. Variable relative humidity-X-ray diffraction ("RH-XRD") experiments have shown that the powder pattern remains unchanged on exposure to different humidities at 25° C.

Polymorphism

Figure 2:
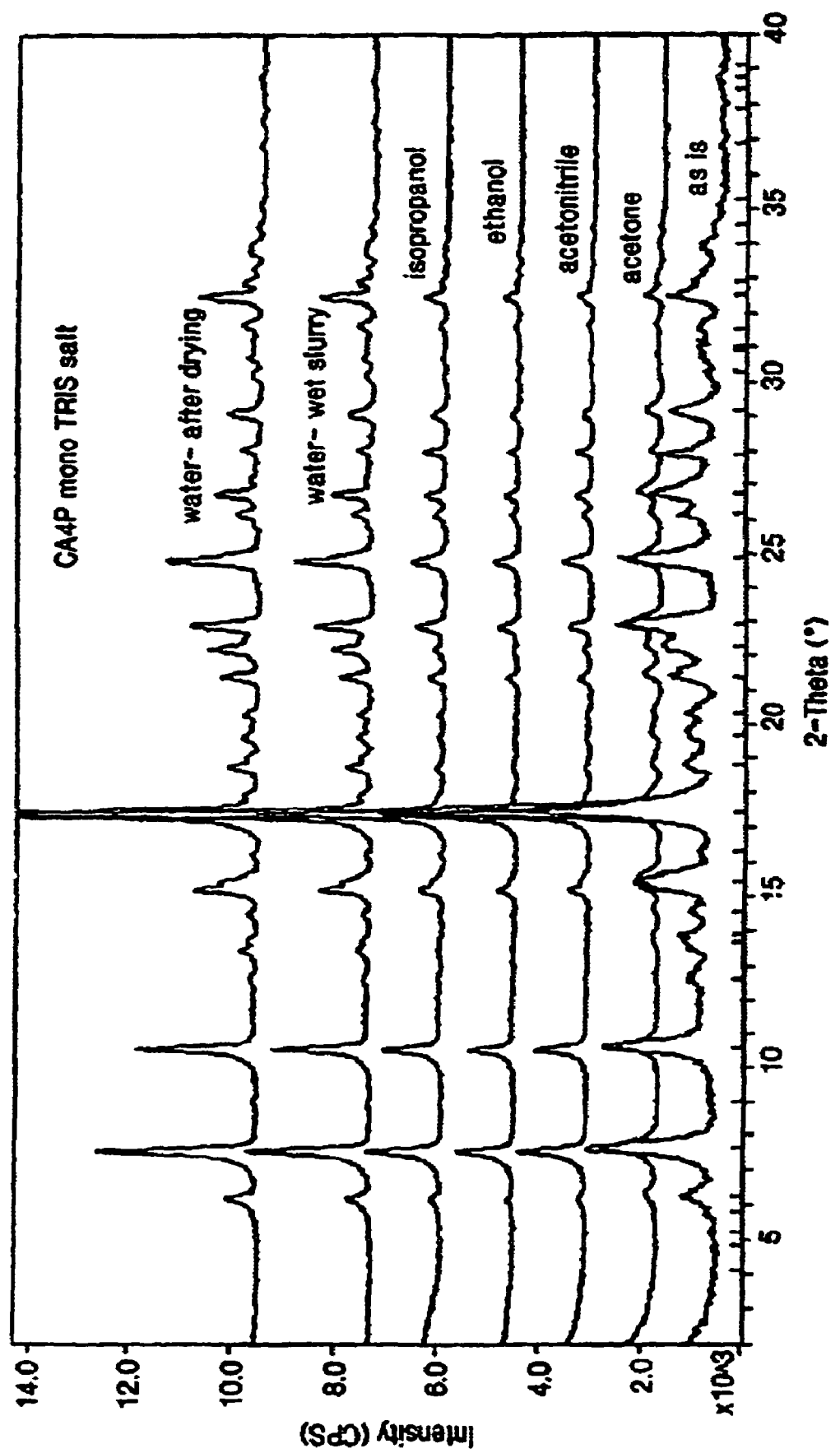
FIG. 2 shows the powder X-ray diffraction patterns of samples of the mono-TRIS salt of CA4P (prepared in Example 1), which were slurried in different solvents (water, isopropanol, ethanol, acetonitrile and acetone) initially at 70 to 75° C. for 5 to 10 minutes, and then at room temperature overnight. The X-ray diffractograms were recorded using a Rigaku Model Miniflex X-ray diffractometer with a Cu-Kα source at a scan rate of 1° per minute from 2° to 40° 2θ.

Single crystal X-ray studies on the CA4P mono TRIS salt of this Example demonstrate that it is an achiral neat form (N-1), which does not contain any solvent sites, and that it has a centrosymmetric monoclinic crystal structure. The simulated powder pattern, which was derived from the refined atomic parameters in the monoclinic single crystal structure at room temperature, is consistent with the observed powder pattern. Several lots of the mono TRIS salt prepared from IPA/water were found to be reproducible based on $^{1}$H NMR, differential scanning calorimetry (DSC), thermogravimetry (TGA) and powder X-ray diffraction (p-XRD). The CA4P mono TRIS salt was slurried in several different solvents such as ethanol, isopropanol acetone, acetonitrile and water, initially at 70-75° C. for 5-10 min, and then at room temperature overnight. The resulting solid phases were analyzed by DSC, TGA and p-XRD. None of the slurried samples showed the presence of any solvates in either the slurry or dry states. There were no differences in the DSC thermograms and the p-XRD patterns (see FIG. 2) in any of these samples as compared to the "as is" material. This indicates that this N-1 form is a relatively stable, single polymorph form.

Other Physicochemical Properties

Figure 3:
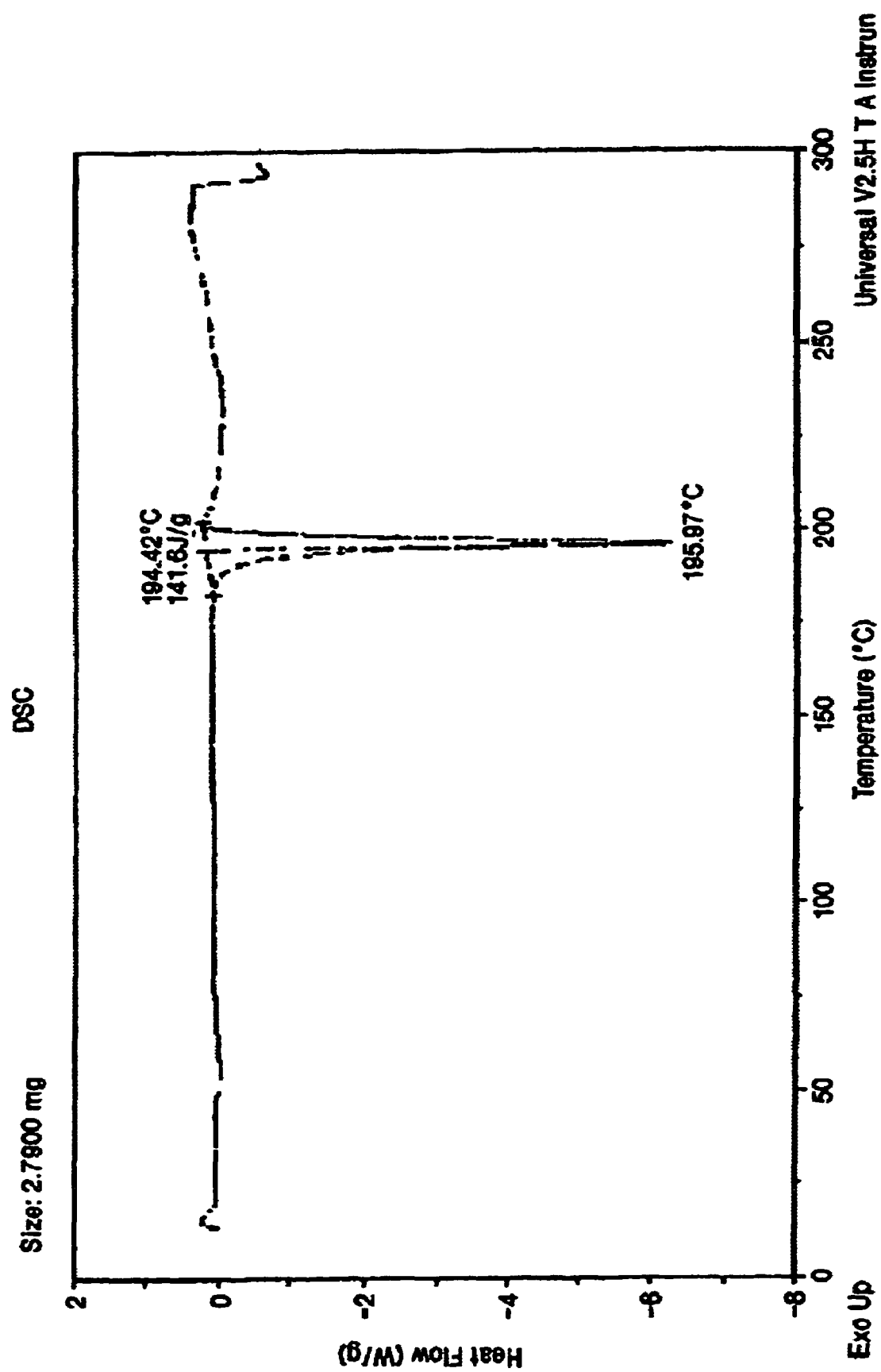
FIG. 3 shows the differential scanning calorimetry (DSC) thermogram (Model DSC 2910, TA instruments) of the mono-TRIS salt of CA4P (prepared in Example 1) obtained under flow of nitrogen with a heating rate of 10 degrees per minute.
Figure 4:
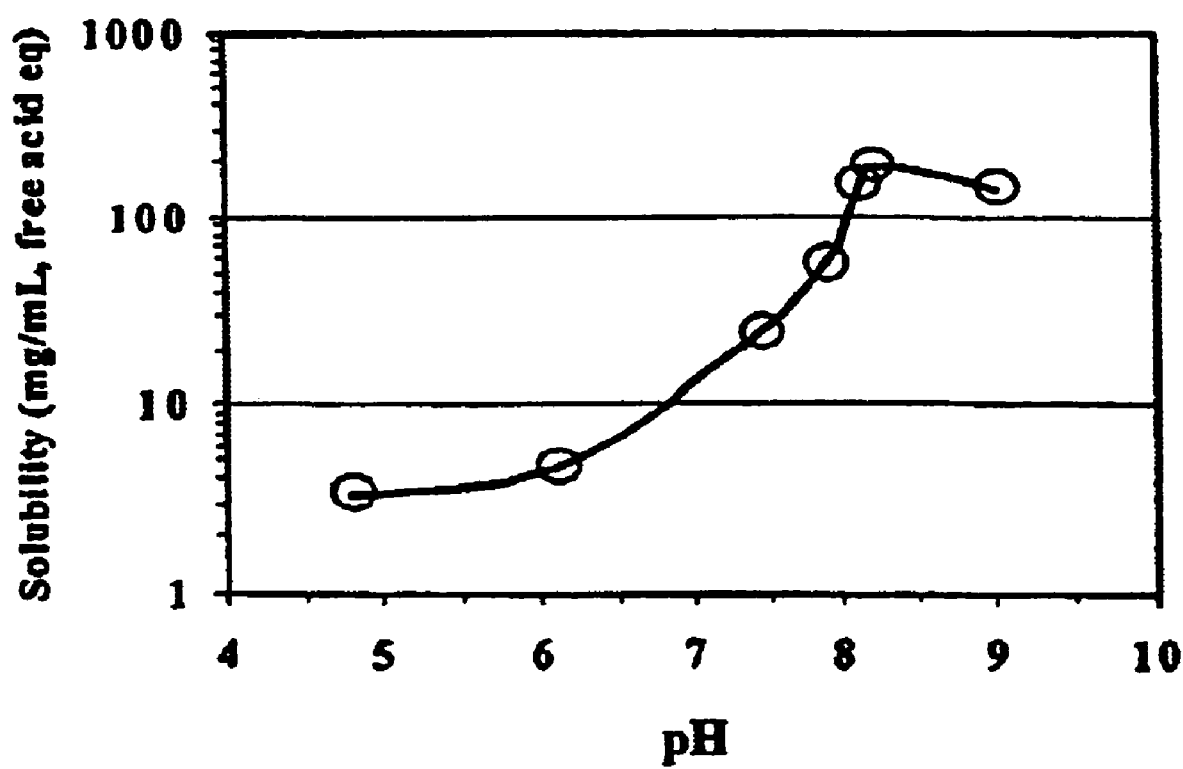
FIG. 4 shows the pH-solubility profile of the mono-TRIS salt of CA4P (prepared in Example 1) at 25° C. The pH was adjusted with sodium hydroxide.

The DSC thermogram of CA4P mono TRIS salt shows a single melt endotherm at 196° C. (FIG. 3). Thermogravimetric analysis did not reveal any weight losses below 150° C. due to volatilization. The equilibrium aqueous solubility of the CA4P mono TRIS salt at 25° C. was determined to be 3.37 mg/mL (pH 4.8). The aqueous solubility increases with an increase in pH and attains a value of 191 mg/mL at pH 8.2. This is especially suitable for preparing a dosage form of the compound of this Example in the pH range 8-9 (including, but not limited to solutions to be directly administered to a patient ("Ready-to-Use Solutions"), or batching solutions for lyophilization) for intravenous administration. The pH-solubility profile of CA4P mono TRIS salt is shown in FIG. 4. The mono TRIS salt also exhibited good chemical stability in the solid-state on exposure to ambient and accelerated conditions of temperature and humidity.

The mono TRIS salt of CA4P of this Example thus has excellent physicochemical properties for use in a pharmaceutical formulation, for example, intended for either oral or parenteral administration. Unlike other salt forms of CA4P not contemplated herein, the mono TRIS salt showed unexpectedly superior properties in the solid-state, particularly the practically nonhygroscopic behavior. This was especially surprising in view of the degree of water solubility of TRIS per se.

CA4P Mono-Tromethamine Salt (Scale-Up)

CA4P free acid solution in IPA. A 12-L three-neck round-bottom flask was equipped with a mechanical stirrer and an additional funnel. A solution of CA4P disodium salt (99.92 g, 0.227 mol) in 1.5 L of deionized water and ethyl acetate (2.0 L) were added to the flask. A solution of hydrochloric acid (0.5 N, 950 mL, 0.475 mol) was added slowly via the additional funnel with rapid stirring (the final pH of the aqueous phase was ca. 1 (pH paper)). The organic phase was separated. The aqueous phase was extracted with ethyl acetate (5×1.6 L). The combined organic phases were dried over $Na_2SO_4$. The ethyl acetate was rotary evaporated to form a thick oil which was dissolved in IPA (800 mL).

CA4P mono-TRIS salt. A solution of TRIS (25.0 g, 0.206 mol) in 800 mL of deionized water was charged to a 12-L three-neck round-bottom flask. CA4P free acid solution in IPA prepared above was added slowly via an additional funnel with rapid stirring. After addition, the resulting solution was seeded with CA4P mono-TRIS salt and mechanically stirred at RT for 1 h. Then, more IPA (2.0 L) was slowly added to the slurry and stirring was continued for another 1 h. The crystalline white solid was isolated by filtration with suction, washed with IPA (800 mL), and dried in a vacuum oven at about 40° C. for 4 days to give 101.55 g of CA4P mono-TRIS salt. The results of the $^1$H NMR analysis of the final product showed that it contained IPA (0.4 wt %) as a residual solvent (0.196 mol, 86% overall yield). Anal. Calcd for $C_{22}H_{32}NO_{11}P$: C, 51.06; H 6.23; N, 2.70; P, 5.98. Found: C, 50.95; H, 6.14; N, 2.69; P, 5.82.

Example 2

CA4P Prodrug Mono-Tromethamine Salt TRIS Formulation

Aqueous solution and lyophile (i.e., freeze dried) pharmaceutical compositions of the compound of Example 1 (CA4P mono TRIS salt) were prepared as follows.

An aqueous solution of the compound of Example 1 was obtained by dissolving the compound in Water for Injection, USP to a concentration of 60 mg/mL with the addition of a sufficient amount of TRIS (tromethamine base) to obtain a pH of 8.5. The dissolution was carried out under the protection from light.

A lyophile was then obtained by the following procedure. The solution formed above was filtered through a suitable 0.2 micron sterilizing filter and aliquoted into sterile glass vials. The solution was lyophilized in a Virtis Lyophilizer at -35° C. under high vacuum over a period of 24 to 72 hours and then further dried at 5° C. under high vacuum for 24 to 48 hours to yield a lyophile.

Other pharmaceutical compositions containing the compound of Example 1 can be prepared in accordance with these procedures. For example, as described above, bulking agents (e.g., amino acids such as arginine, or lysine, sugars such as sucrose, lactose, mannitol, polymers such as polyvinylpyrrolidones or dextran, etc.) or other excipients can be added to the above solution.

For example, an aqueous solution of the compound of Example 1 was obtained by dissolving the compound in Water for Injection, USP to a concentration of 30 mg/mL with the addition of a suitable bulking agent such as mannitol, dextran, or combinations thereof to a concentration of 100 mg/mL and a sufficient amount of TRIS (tromethamine base) to obtain a pH of 8.6. The dissolution was carried out under the protection from light.

A lyophile was then obtained by the following procedure. The solution formed above was filtered through a suitable 0.2 micron sterilizing filter and aliquoted into sterile glass vials. The solution was lyophilized in a Virtis Lyophilizer at -10° C. under moderate vacuum over a period of 24 to 72 hours and then further dried at 5° C. under high vacuum for 24 to 48 hours to yield a lyophile.

As explained above, any suitable organic amines including, but not limited to diethanolamine, glucamine, N-methylglucamine, ethylenediamine, and 2-4-imidazolyl) ethyl amine, can readily be substituted for tromethamine in the Examples described above to produce a compound or composition of the present invention. Compositions wherein Q has other definitions within formula I can be similarly formed.

Example 3

CA4P Mono-L-Histidine Salt Prodrug

In an embodiment of the present invention, a CA4P mono-L-histidine salt is described as a non-limiting example of a compound of the present invention. With the information described herein, one of ordinary skill in the art can readily produce a variety of CA4P mono- or di-amino acid salt prodrugs, such as by addition of the desired amino acid to CA4P free acid by a procedure analogous to that described following, all of which are encompassed by the present invention and the appended claims.

Reagents and Methods

The following reagents and chemicals were obtained from commercial sources and used without further purification: L-Histidine (Aldrich Chemical Co. 98% labeled, Lot #04821JR), methanol and isopropyl alcohol (B&J Brand, High purity solvent grade). "CA4P disodium salt" is the compound having the following structure:

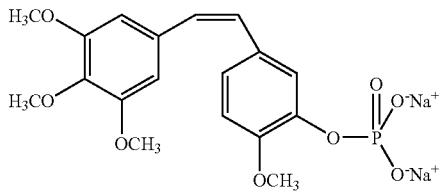

(See U.S. Pat. No. 5,561,122 mentioned above).

Multi-nuclei NMR spectra were recorded on Bruker DPX 300 and DRX 400 spectrometers. The $^1$H and $^{13}$C NMR chemical shifts are reported in ppm relative to tetramethylsilane (the $^{13}$C NMR chemical shifts were determined using methanol as external standard). The $^{31}$P NMR chemical shifts are reported in ppm relative to 85% $H_3PO_4$ (external standard). The $^{13}$C and $^{31}$P NMR spectra were acquired with proton decoupled {$^1$H}. The 2D NMR experiments (HMQC and HMBC) were conducted to aid the assignments of the $^1$H and $^{13}$C NMR signals to the structure. DSC were performed on DSC/2920 Differential Scanning Calorimeter, TA Instruments.

CA4P Mono-L-Histidine Hydrated Salt

L-Histidine aqueous stock solution (0.2 M). L-Histidine (0.3167 g, 2.0 mmol) was dissolved in 10 mL of deionized water to form a 0.2 M solution.

CA4P free acid stock solution in methanol (0.6 M). CA4P disodium salt (1.9194 g) was dissolved in 5.0 mL of deionized water. A sodium chloride saturated aqueous solution (40 mL) was added to the resulting solution. White solid precipitated Ethyl acetate (50 mL) was added and the resulting slurry was magnetically stirred and acidified with a solution of 0.5 N hydrochloric acid until the biphasic mixture became clear (the aqueous phase was acidic (pH paper)). The organic phase was separated. The aqueous phase was extracted with ethyl acetate (2×50 mL). The organic phases were combined and dried over $Na_2SO_4$. Filtration and solvent evaporation (rotavapor, water bath temperature=37° C.) yielded a thick film of CA4P free acid which was taken up with 10 mL of methanol. The methanol was rotary evaporated (37° C.) to give an off-white foam (152 g), which was re-dissolved in MeOH (4.79 mL) to yield a solution with an expected 0.8 M concentration.

The concentration determined above was further confirmed by mixing 100 μL of a 0.2 M histidine solution (20 μmol) with 25 μL of CA4P free acid solution. The solvents of the resulting solution were rotary evaporated to dryness. The solid was analyzed by $^1$H NMR to show a 1:0.75 mole ratio of histidine: CA4P free acid. Therefore, the concentration of CA4P free acid was figured out as 0.6 M. (Thus result indicated that the foam of CA4P free acid contained solvent).

CA4P mono-L-histidine hydrated salt. To a 4-mL HPLC vial were added L-histidine (900 μL, 0.2 M, 180 μmol), CA4P free acid (300 μL, 0.6 M, 180 μL), and isopropyl alcohol (1.0 mL). The resulting solution was rotary evaporated (water bath temperature=39-40° C.) to reduce the volume down to ca 1.5 mL. Another 1.0 mL of isopropyl alcohol was added and the volume was further reduced to ca. 15 mL. A small crystal was observed in the solution. The evaporation process was stopped and the vial was capped and allowed to stand at ambient temperature for 5 h. The crystalline solid was isolated by filtration through a Whatman #54 filter paper with suction, washed with isopropyl alcohol (ca. 2 mL), and dried in a stream of nitrogen overnight to yield 82.7 mg of CA4P mono-L-histidine as a white solid. The CA4P mono-L-histidine salt prodrug obtained was a crystalline solid; Karl Fisher analysis of the solid showed that the water content was 4.66%, which calculated to a crystalline solid hydrated with 1.5 water molecules per salt molecule (143 μmol, 79% yield): $^1$H NMR (300 MHz, $D_2O$) δ 3.33 (d, J=6.59 Hz, 2H, C(21)$H_2$), 3.67 (s, 6H, C(15)$H_3$ and C(17)$H_3$), 3.74 (s, 3H, C(16)$H_3$), 3.82 (s, 3H, C(18)$H_3$), 4.01 (t, J=6.50 Hz, 1H, C(20)H), 6.53 (d, J=12.25 Hz, 1H, C(8)H, 6.62 (d, J=12.25 Hz, 1H, C(7)H), 6.62 (s, 2H, C(10)H and C(14)H), 6.94 (d, J=8.00 Hz, 1H, C(3)H), 7.01 (d, J=8.00 Hz, 1H, C(4)H), 7.21 (s, 1H, C(6)H), 7.37 (s, 1H, C(23)H, 8.63 (s, 1H, C(24)H; $^{13}$C NMR (100 MHz, {$^1$H}, $D_2O$) δ 26.12 (C21), 53.93 (C20), 56.26 (2C, C15, C17), 56.35 (C18), 61.32 (C16), 106.86 (2C, C10, C14), 113.26 (C3), 118.03 (C23), 122.04 (d, $J_{PC}$=2.3 Hz, C6), 125.52 (C4), 127.80 (C22), 129.40 (C8), 130.05 (C7), 130.57 (C5), 133.99 (C9), 134.34 (C24), 136.18 (C12), 141.37 (d, $J_{PC}$=6.90 Hz, C1), 150.01 (d, $J_{PC}$=4.60 Hz, C2), 152.52 (2C, C11 and C13), 172.87 (C19); $^{31}$P NMR (121 MHz, {$^1$H}, $D_2O$) δ -2.61(s). Anal. Calcd for $C_{24}H_{30}N_3O_{10}P$.1.5 $H_2O$: C, 49.83; H 5.75; N, 726. Found: C, 50.13; H, 5.78; N, 7.26.

Figure 5:
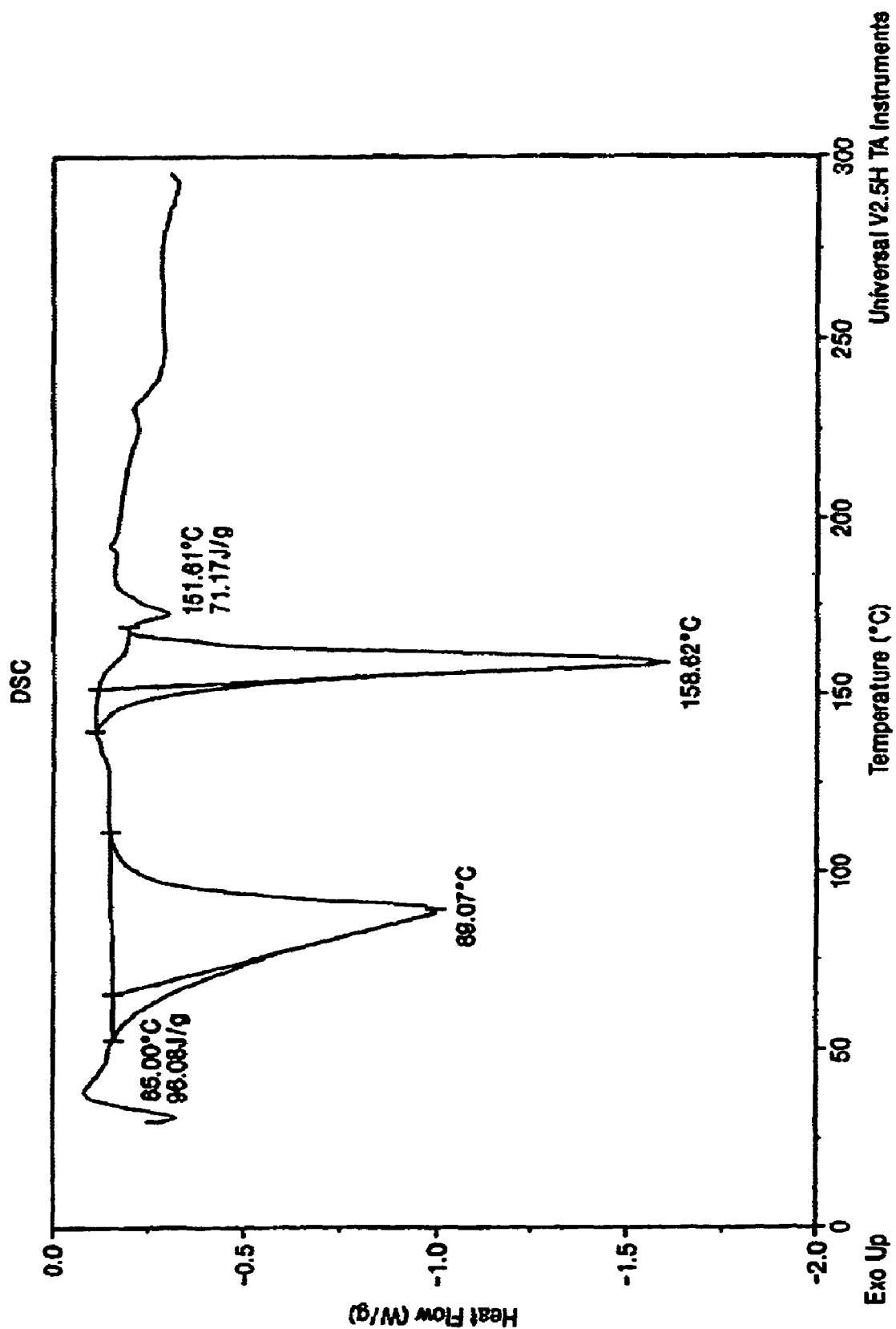
FIG. 5 shows the differential scanning calorimetry (DSC) thermogram of the mono-L-histidine salt of CA4P (prepared in Example 3) (2.0900 mg sample size).
Figure 8:
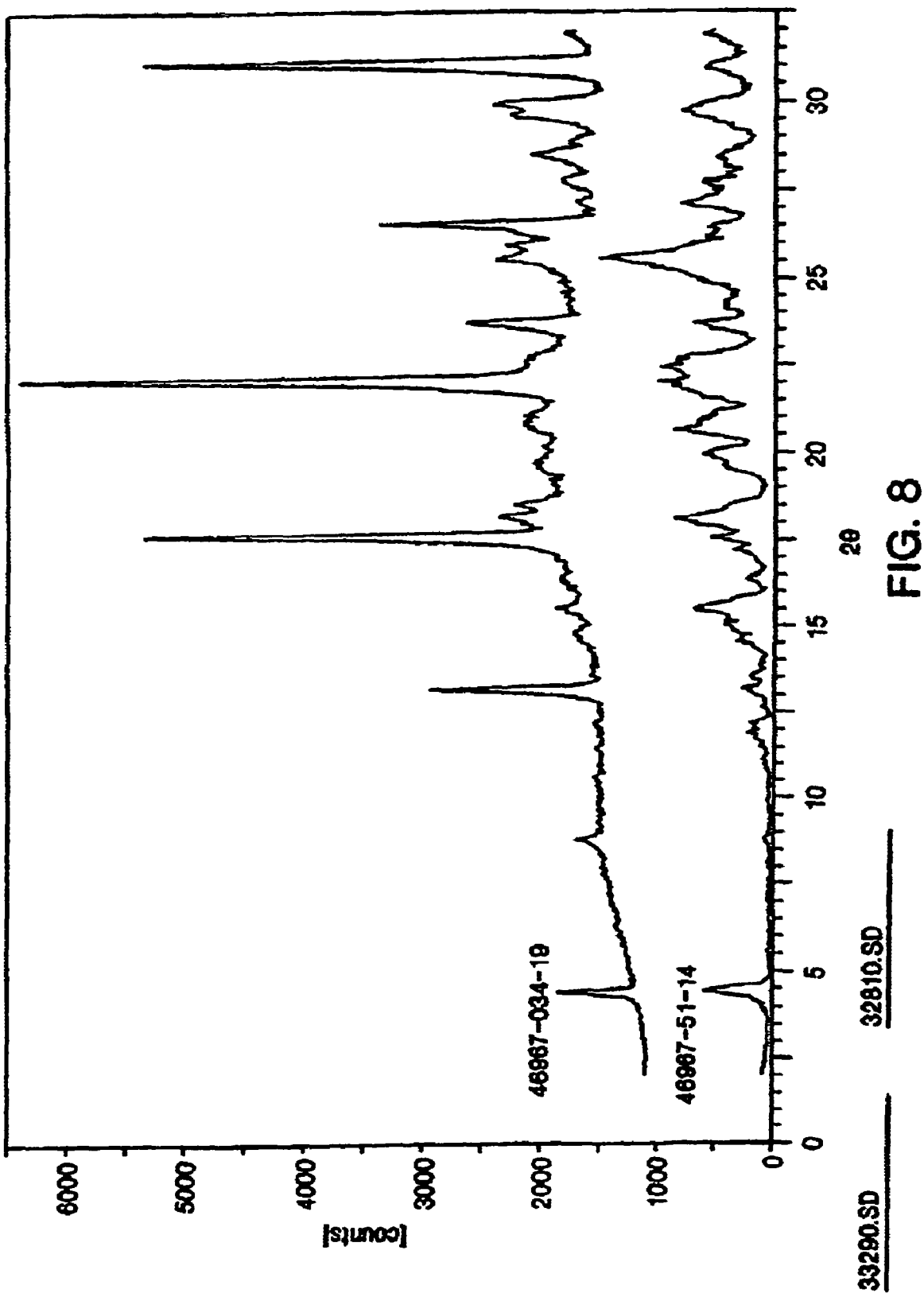
FIG. 8 shows the powder X-ray diffraction patterns of the mono-L-histidine salt of CA4P (prepared in Example 3).

The Karl Fisher and elemental analyses of the product of this procedure showed that the crystalline salt is sesquihydrate. The DSC analysis indicated one major crystalline form with a melting endotherm at 158.6 deg C. (see FIG. 5). The powder X-ray data obtained for this material is shown in FIG. 8, top pattern.

Figure 6:
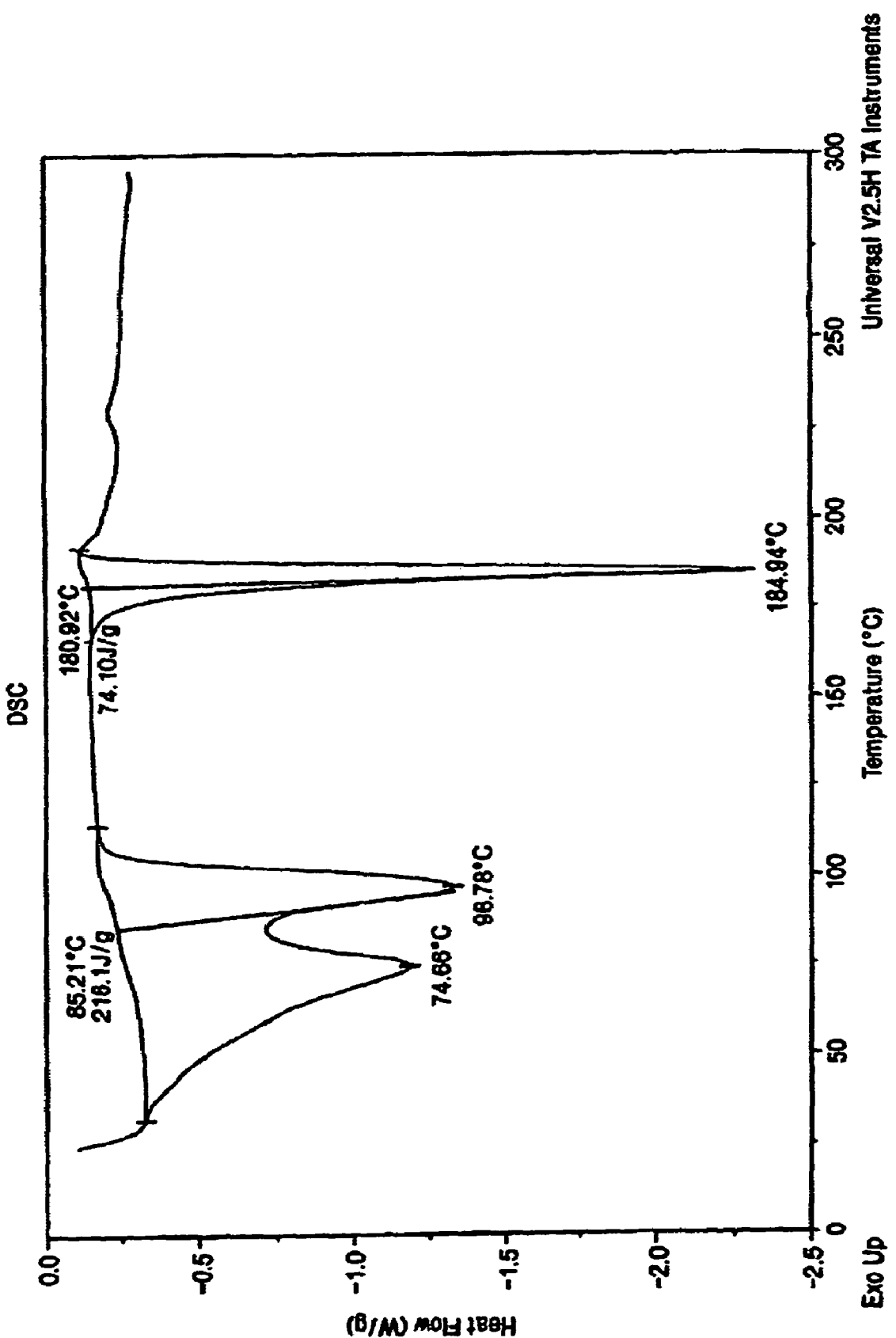
FIG. 6 shows the differential scanning calorimetry (DSC) thermogram of the mono-L-histidine salt of CA4P (prepared in Example 3).
Figure 7:
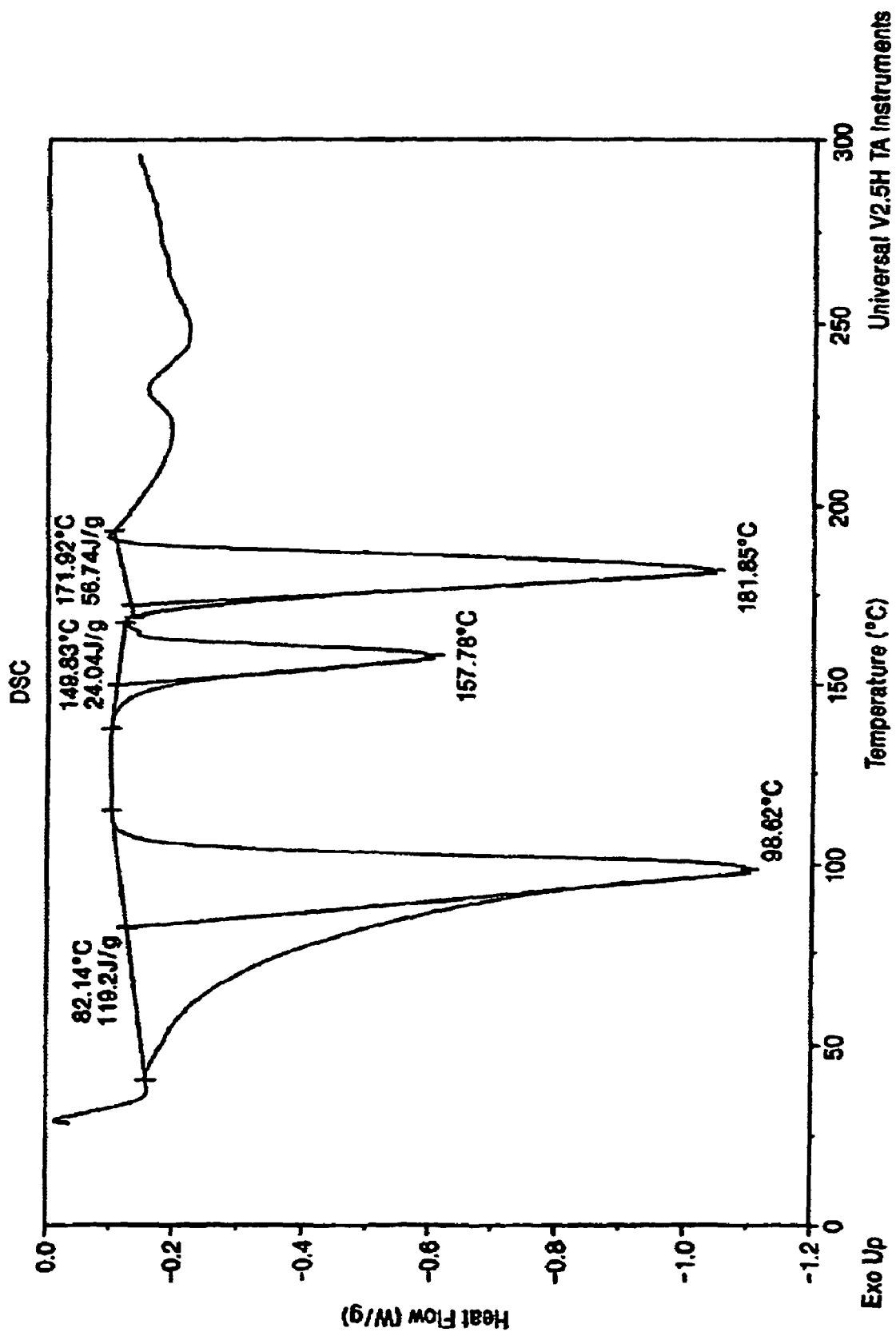
FIG. 7 shows the differential scanning calorimetry (DSC) thermogram of the mono-L-histidine salt of CA4P (prepared in Example 3).
Figure 9:
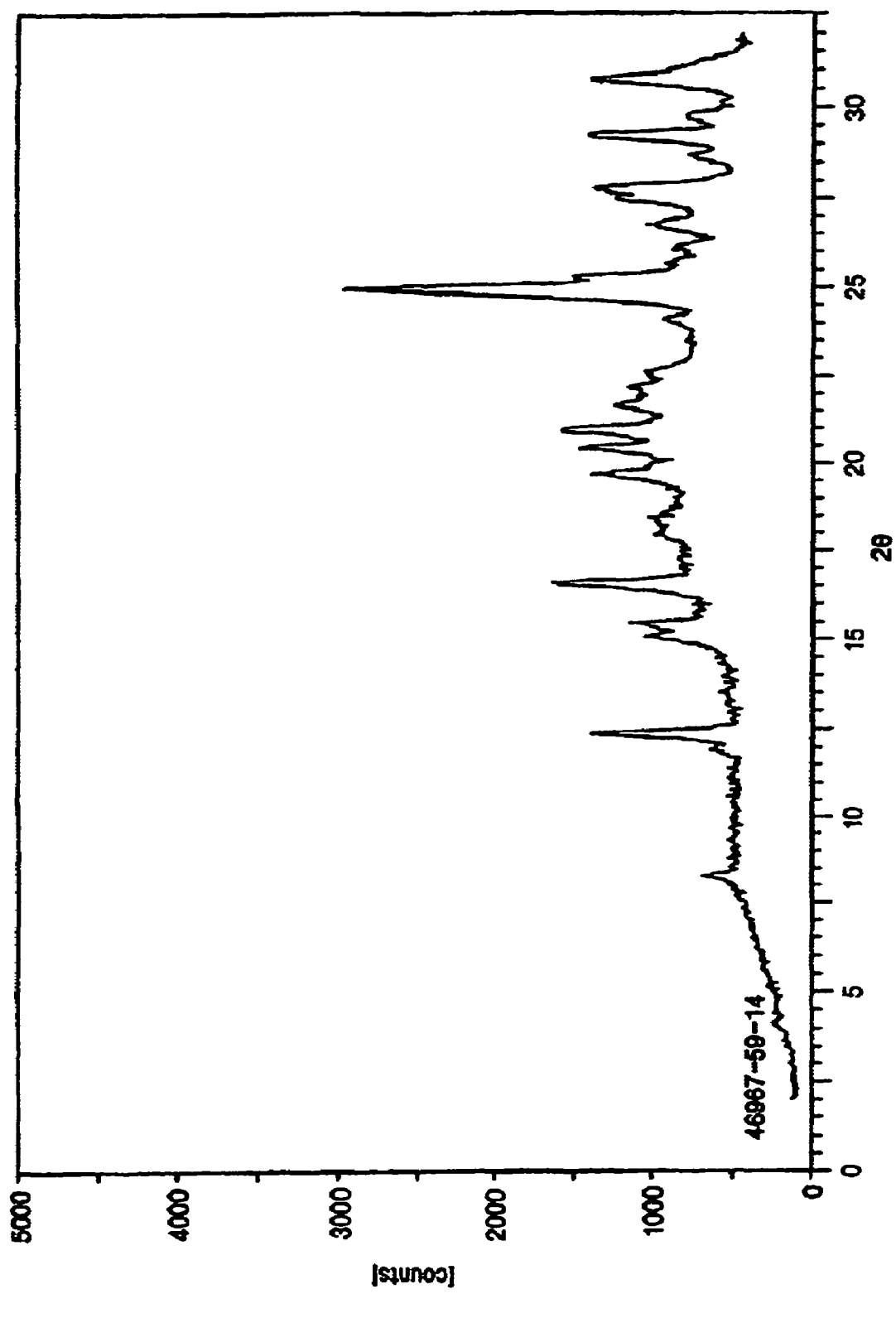
FIG. 9 shows the powder X-ray diffraction patterns of the mono-L-histidine salt of CA4P (prepared in Example 3).

Differences of polymorphism were observed, at room temperature, as a function of mmoles of CA4P free acid relative to the total volume of the crystallization mixture. In the above procedure, 0.2 mmoles of CA4P free acid per ml of the total volume of the crystallization mixture were employed. Modification of the above procedure such that 0.03 mmoles of CA4P free acid per ml of the total volume of the crystallization mixture were employed provided a CA4P mono-L-histidine salt form having 1.8 molecules of water per molecule of salt (see FIG. 6, sample size 3.8500 mg; the DSC analysis showed one crystalline form with a melthing endotherm at 184.9 deg C. $^1$H NMR analysis showed the ratio of CA4P: histidine=1:1). The powder X-ray data obtained for this material is shown in FIG. 8, bottom pattern. Another modification of the above procedure such that 0.07 mmoles of CA4P free acid per ml of the total volume of the crystallization mixture were employed provided a mixture of CA4P mono-L-histidine salt forms, one having 1.5 molecules of water per molecule of salt, and the other having 1.8 molecules of water per molecule of salt (see FIG. 7, sample size 4.4500 mg; the Karl Fisher and elemental analyses of this mixture showed that the crystalline salt is sesquihydrate. The DSC analysis illustrated two crystalline forms. The endotherms are similar to those of FIGS. 5 and 6, respectively. The powder X-ray data obtained for this material is shown in FIG. 9. The DSC and powder X-ray data indicated that the 1.5:1 and 1.8:1 (water:salt) forms above are two different crystalline forms. As also noted above, a mixture of these two forms is easily formed. With seeding, each form can be made in a pure state.

The hemiheptahydrate CA4P mono-L-histidine salt form can also be obtained in the presence of water. This form, however, converts to the sesquihydrate CA4P mono-L-histidine salt form.

As explained above, a variety of natural or non-natural amino acids including, but not limited to ornithine, lysine, arginine, and tryptophan can readily be substituted for histidine in the description described above to produce a compound of the present invention.

CA4P Mono-L-Histidine Hydrated Salt (Scale-Up)

L-histidine aqueous stock solution (0.2 M). L-Histidine (1.90 g, 12.0 mmol) was dissolved in 60 mL of deionized water to form a 0.2 M solution. (This solution can also be prepared in situ).

CA4P free acid stock solution in isopropyl alcohol (IPA) (0.17 M). CA4P free acid can be prepared in the following manner. The acid equivalent can be reduced to 2.1; the addition of sodium chloride is not necessary. The following procedure is exemplary: CA4P disodium salt (8.94 g, 20.3 mmol) was dissolved in 50 mL of deionized water. Ethyl acetate (200 mL) and a saturated aqueous sodium chloride solution (100 mL) were added to the resulting solution with rapid stirring. A white cake was formed. A solution of 0.5 N hydrochloric acid (220 mL) was added portion-wise to dissolve the cake (the final pH of the aqueous phase was ca. 1 (pH paper)). The organic phase was separated. The aqueous phase was extracted with ethyl acetate (1×200 mL and then 2×150 mL). The organic phases were combined and dried over $Na_2SO_4$. Filtration and solvent evaporation (rotavapor, water bath temperature=40° C.) yielded a thick film of CA4P free acid which was dissolved in 100 mL of IPA. The concentration of the resulting solution was determined to be 0.17 M by $^1$H NMR.

In order to confirm the concentration determined above, 60 μL of histidine solution (0.2 M) and 70 μL of CA4P free acid solution were pipetted into a 4-mL HPLC vial. The solvents were rotary evaporated to dryness. The solid was dissolved in 0.7 mL of $D_2O$ and analyzed by $^1$H NMR to give a 1:1 ratio of histidine to CA4P free acid. A total of 17 mmol of CA4P free acid was obtained (84% yield).

CA4P mono-L-histidine hydrated salt (scale-up). A 250-mL round bottom flask was charged with 70.6 mL of CA4P free acid solution (0.17 M, 12.0 mmol) and 50 mL of IPA. A solution of L-histidine (60 mL, 0.2 M, 12.0 mmol) was added portion-wise to the CA4P free acid solution with rapid stirring. The resulting white slurry was stirred at 40° C. for 30 min, at ambient temperature for 3 h, followed by cooling to 0° C. (ice-bath) for 1 h. The crystalline solid was isolated by filtration through a Whatman #54 filter paper with suction, washed with cold isopropyl alcohol, and dried in vacuo (vacuum desiccator) for 88 h to yield 6.07 g of CA4P mono-L-histidine as a white solid. Karl Fisher analysis of the solid showed that the water content was 4.48%, which calculated to a crystalline solid hydrated with 1.5 water molecules per salt molecule (10.5 mmol, 87% yield): $^1$H NMR (300 MHz, $D_2O$) δ 3.32 (d, J=6.6 Hz, 2H, C(21)$H_2$), 3.68 (s, 6H, C(15)$H_3$ and C(17)$H_3$), 3.74 (s, 3H, C(16)$H_3$), 3.82 (s, 3H, C(18)$H_3$), 4.00 (t, J=6.6 Hz, 1H, C(20)H), 6.53 (d, J=12.1 Hz, 1H, C(8)H), 6.62 (d, J=12.1 Hz, 1H, C(7)H), 6.64 (s, 2H, C(10)H and C(14)H), 6.95 (d, J=8.3 Hz, 1H, C(3)H), 7.02 (d, J=8.3 Hz, 1H, C(4)H), 7.20 (broad s, 1H, C(6)H), 7.36 (broad s, 1H, C(23)H, 8.62 (d, J=1.3 Hz, 1H, C(24)H); $^{13}$C NMR (100 MHz, {$^1$H}, $D_2O$) δ 26.11 (C21), 53.92 (C20), 56.22 (2C, C15, C17), 56.32 (C18), 61.28 (C16), 106.82 (2C, C10, C14), 113.20 (C3), 118.03 (C23), 122.01 (d, $J_{PC}$=2.3 Hz, C6), 125.48 (C4), 127.78 (C22), 129.38 (C8), 129.97 (C7), 130.54 (C5), 133.92 (C9), 134.31 (C24), 136.16 (C12), 141.38 (d, $J_{PC}$=6.1 Hz, C1), 149.98 (d, $J_{PC}$=5.4 Hz, C2), 152.48 (2C, C11 and C13), 172.86 (C19). Anal. Calcd for $C_{24}H_{30}N_3O_{10}P \cdot 1.5H_2O$: C, 49.82; H, 5.75; N, 7.26; P, 5.35. Found: C, 49.92; H, 5.84; N, 7.26; P, 5.44. Furthermore, using differential scanning calorimetry, the compound obtained was determined to have a major endotherm at 158° C., and a minor endotherm at 174° C.

Any suitable natural or non-natural amino acid can readily be substituted into this procedure to produce other compounds of the present invention.

When CA4P mono-L-histidine salt is crystallized at room temperature, hydrate(s) are generally obtained. Carrying out the crystallization process at temperatures elevated above room temperature, especially greater than 70° C., allows anhydrous salt to be obtained. Histidine salt hydrates can be converted to the anhydrous crystalline form (especially, melting at 210° C.), for example, by slurrying a hydrate form in a solvent such as ethanol, methanol, isopropanol, or acetone, at a temperature such as 40° C. (such as for 2 days), followed by filtration, washing and vacuum drying at a temperature such as 45° C. (such as overnight). The anhydrous form, which is practically nonhygroscopic, is preferred.

CA4P Mono-L-Histidine Anhydrous Salt

A 200-mL round bottom flask was charged with L-histidine (0.2620 g, 1.65 mmol) and 16.5 mL of deionized water. The resulting solution was heated at 74-76° C. (oil bath temperature) with magnetic stirring. A solution of CA4P free acid (8.7 mL, 0.19 M in IPA, 1.65 mmol) was added, followed by isopropyl alcohol (90 mL). The resulting solution became milky in ca. 1 min. Stirring was continued at 75-76° C. for 2 h and then at ambient temperature for 1 h. The needle crystalline solid was isolated by filtration through a Whatman #4 filter paper with suction and dried in a steam of air (suction) overnight (19.5 h) and in vacuum desiccator for 24 h to yield 0.7788 g of CA4P mono-L-histidine as a white solid (1.41 mmol, 86% yield): mp 211.49° C. (DSC); $^1$H NMR (400 MHz, $D_2O$) δ 3.30 (d, J=6.5 Hz, 2H, H-21), 3.65 (s, 6H, H-15 and H-17), 3.72 (s, 3H, H-16), 3.80 (s, 3H, H-18), 3.99 (t, J=6.5 Hz, 1H, H-20), 6.50 (d, J=12.3 Hz, 1H, H-8), 6.59 (d, J=12.3 Hz, 1H, H-7), 6.60 (s, 2H, H-10 and H-14), 6.92 (d, J=8.5 Hz, 1H, H-3), 6.97 (broad d, J=8.5 Hz, 1H, H-4), 7.19 (broad s, 1H, H-6), 7.33 (broad s, 1H, H-23), 8.58 (broad s, 1H, H-24); $^{13}$C NMR (100 MHz, ({$^1$H}, $D_2O$) δ 27.11 (C-21), 54.88 (C-20), 57.17 (2C, C-15, and C-17), 57.24 (C-18), 62.24 (C-16), 107.77 (2C, C-10 and C-14), 114.17 (C-3), 118.90 (C-23), 122.93 (d, $J_{PC}$=2.3 Hz, C-6), 126.40 (C-4), 128.88 (C-22), 130.29 (C-8), 131.00 (C-7), 131.47 (C-5), 134.93 (C-9), 135.32 (C-24), 137.08 (C-12), 14231 (d, $J_{PC}$=6.1 Hz, C-1), 150.91 (d, $J_{PC}$=4.6 Hz, C-2), 153.45 (2C, C-11 and C-13), 173.84 (C-19). Anal. Calcd for $C_{24}H_{30}N_3O_{10}P$: C, 52.27; H, 5.48; N, 7.62; P, 5.61. Found: C, 52.03; H, 5.43; N, 7.57; P, 5.57.

CA4P Mono-L-Histidine Anhydrous Salt (scale-Up)

A 2000-mL three-neck round-bottom flask was equipped with a mechanical stirrer, a 500-mL additional funnel, and a thermocouple which was connected to a Thermo-O-Watch L7-1100SA/28T which controlled a heating mantle. L-histidine (3.42 g, 21.6 mmol) was added to the flask, followed by 216 mL of deionized water. The resulting solution was heated at 74-80° C. with stirring. CA4P free acid (120 mL, 0.18 M in IPA, 21.6 mmol) was added, followed by IPA (1176 mL), via the additional funnel in a rate to maintain the solution temperature at 73-74° C. (14 min required). After the addition of IPA, the resulting clear solution was seeded with CA4P mono-L-histidine anhydrous salt (trace amount). The solution temperature was increased to 80° C., and crystallization took place in ca. 3 min after seeding. The temperature dropped down slowly to 74° C. over 30 min and was maintained at 73-74° C. for another 1.5 h. The reaction mixture was allowed to cool down slowly to 31° C. in 3.5 h. The needle crystalline solid was filtered over a Whatman #4 filter paper with suction, washed with IPA (100 mL), and dried in a stream of air (suction) overnight (16 h) and in a vacuum dessicator for 21.5 h to yield 10.11 g of CA4P mono-L-histidine anhydrous salt as white solid (18.3 mmol 85% yield): mp 213.65° C. (DSC); $^1$H NMR (400 MHz, $D_2O$) δ 3.30 (d, J=6.5 Hz, 2H, H-21), 3.65 (s, 6H, H-15 and H-17), 3.72 (s, 3H, H-16), 3.80 (s, 3H, H-18), 3.99 (t, J=6.5 Hz, 1H, H-20), 6.49 (d, J=12.0 Hz, 1H, H-8), 6.58 (d, J=12.0 Hz, 1H, H-7), 6.59 (s, 2H, H-10 and H-14), 6.91 (d, J=8.5 Hz, 1H, H-3), 6.97 (dd, J=8.3, 1.7 Hz, 1H, H-4), 7.19 (broad t, J=1.7 Hz, 1H, H-6), 7.34 (broad s, 1H, H-23), 8.60 (d, J=1.4 Hz, 1H, H-24); $^{13}$C NMR (100 MHz, $\{^1H\}$, $D_2O$) δ 27.07 (C-21), 54.86 (C-20), 57.18 (2C, C-15 and C-17), 57.26 (C-18), 62.24 (C-16), 107.78 (2C, C-10 and C-14), 114.18 (C-3), 118.94 (C-23), 122.95 (d, $J_{PC}$=2.3 Hz, C6), 126.43 (C-4), 128.79 (C-22), 130.31 (C-8), 130.98 (C-7), 131.49 (C-5), 134.91 (C-9), 135.29 (C-24), 137.10 (C-12), 142.31 (d, $J_{PC}$=6.9 Hz, C-1), 150.92 (d, $J_{PC}$=4.6 Hz, C-2), 153.45 (2C, C-11 and C-13), 173.82 (C-19). Anal. Calcd for $C_{24}H_{30}N_3O_{10}P$: C, 52.27; H, 5.48; N, 7.62; P, 5.61. Found: C, 52.23; H, 5.35; N, 7.60; P, 5.55.

Figure 10:
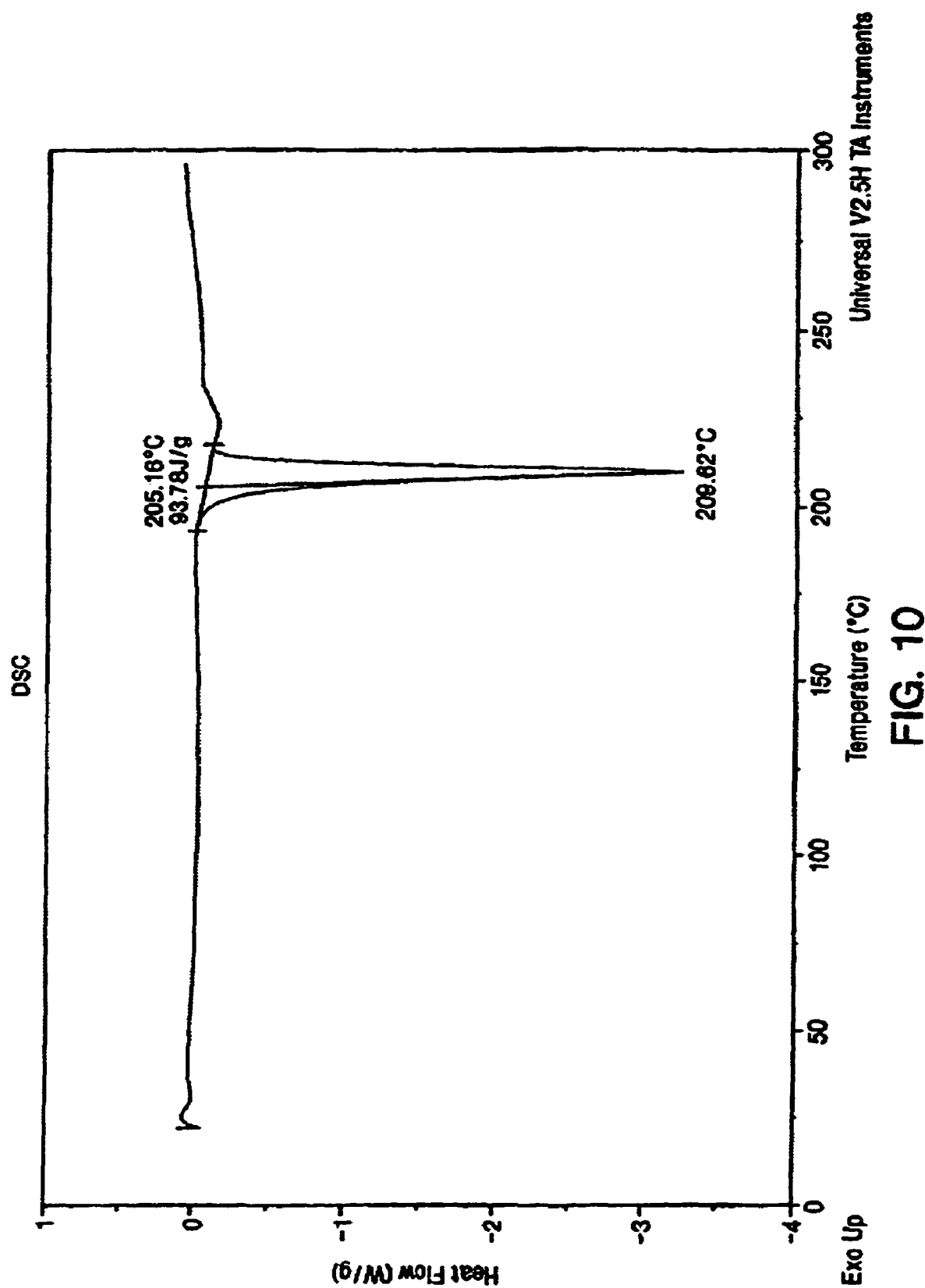
FIG. 10 shows the differential scanning calorimetry (DSC) thermogram of the mono-L-histidine anhydrous salt of CA4P (prepared in Example 3).
Figure 11:
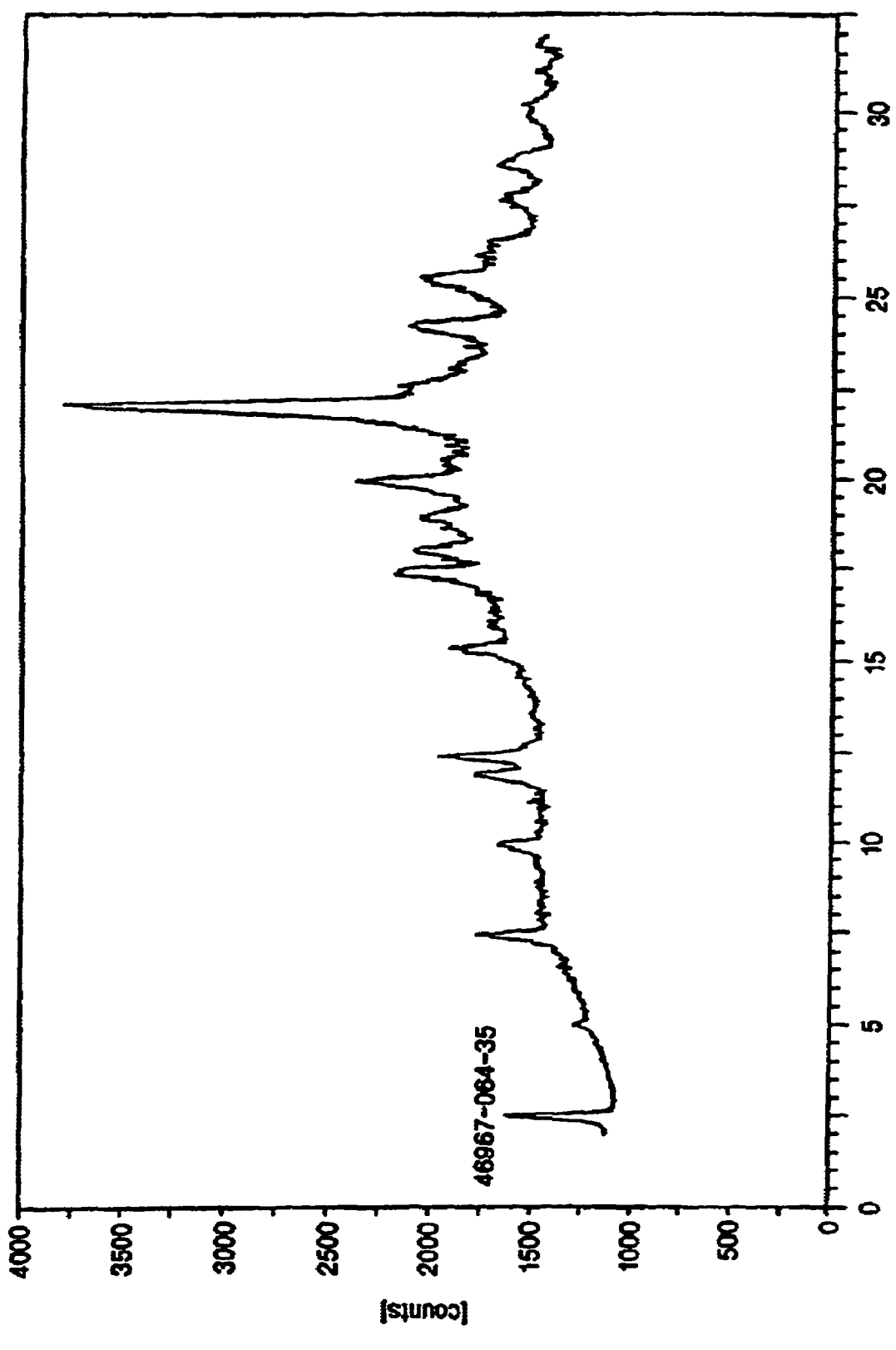
FIG. 11 shows the powder X-ray diffraction patterns of the mono-L-histidine anhydrous salt of CA4P (prepared in Example 3).

The CA4P mono-L-histidine anhydrous salt can be made reproducibly as a single crystalline form. FIG. 10 shows the DSC (sample size 2.3600 mg); FIG. 11 shows the powder X-ray data for this material.

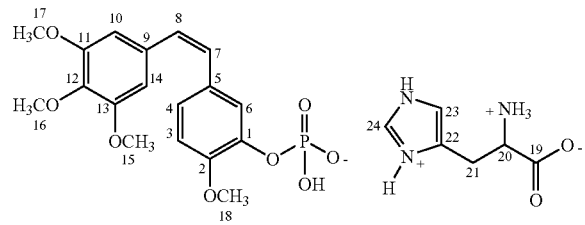

Example 4

Preparation of cis-CA4P Monoglycine Methyl Ester Salt

The following procedure for the preparation of CA4P monoglycine methyl ester from CA4P disodium is advantageous. The procedure employs glycine methyl ester hydrochloride directly in the presence of N,N-diisopropylethylamine, providing enhanced stability as compared with preparation employing glycine methyl ester free base. Furthermore, the preparation of CA4P free acid is improved significantly—concentrated sulfinic acid is employed (rather than, for example, diluted hydrochloride acid) in neutralization (as a result, the use of, for example, ethyl acetate for extraction and then evaporation is eliminated). The formation of trans-CA4P free acid is avoided in this improved procedure.

Reagents and Method

The following reagents and chemicals were obtained from commercial sources and used without further purification: Isopropyl alcohol (IPA) (B&J Brand, High purity solvent grade), sulfuric acid (EM Science, 95-98%, Lot #35310), glycine methyl ester hydrochloride (Aldrich Chemical Co. 99% labeled, Lot #03214 MU), N,N-diisopropylethylamine (Aldrich Chemical Co. 99.5% labeled, Lot #02819 ER). Multi-nuclei NMR spectra were recorded on Bruker DRX 400 spectrometer. The $^1$H and $^{13}$C NMR chemical shifts are reported in ppm relative to tetramethylsilane (The $^{13}$C NMR chemical shifts were determined using MeOH as external standard). The 2D NMR experiments [HMQC (Heteronuclear Multiple Quantum Correlation spectroscopy, an inverse chemical shift correlation experiment to determine which $^1$H's of the molecule are bonded to which $^{13}$C nuclei (or other X nuclei)]; and HMBC (Heteronuclear Multiple Bond Correlation spectroscopy, a modified version of HMQC suitable to determine long-range $^1$H-$^{13}$C connectivity, as well as the structure and $^1$H and $^{13}$C assignments of the molecule)) were conducted to aid the assignments of the $^1$H and $^{13}$C NMR signals to the structure. Differential scanning calorimetry (DSC) was performed on DSC 2920 Differential Scanning Calorimeter, TA Instruments.

Cis-CA4P Monoglycine Methyl Ester Salt

A 100-mL round-bottom flask was charged with cis-CA4P disodium salt (2.866 g, 6.51 mmol) and EPA (30 mL). The resulting slurry was magnetically stirred at ambient temperature. A solution of sulfuric acid (0.365 mL, 6.51 mmol) in IPA (60 mL) was added portionwise to the slurry. The mixture was continuously stirred for about 10 min and filtered with suction using a Whatman #1 filter paper. The solid ($Na_2SO_4$ which is insoluble in IPA) was washed with IPA (10 mL). The filtrate and wash, which contained CA4P free acid, were combined in another 100-mL round-bottom flask. Glycine methyl ester hydrochloride (0.826 g, 6.51 mmol) and N,N-diisopropylethylamine (1.254 mL, 7.16 mmol) were added to the combined solution. The resulting mixture was heated in an oil bath with magnetically stirring. At 60° C., the mixture became a clear solution. At 65° C., the solution became slurry. At 78° C., the slurry dissolved to form a clear solution. Heating was stopped and the solution was allowed to cool down slowly in the oil bath. At 60° C., the seed of cis-CA-4P monoglycine methyl ester salt was added to the solution to form a slurry. Stirring was continued from 60° C. to ambient temperature for about 1 h and then at ambient temperature overnight. The white crystalline solid was isolated by filtration with suction using a Whatman #1 filter paper and washed with IPA (3×10 mL) and dried in a stream of air for 6 h to give 2.609 g of cis-CA4P monoglycine methyl ester salt (5.38 mmol, 82.6% yield): HPLC analysis, 100% cis-CA4P; mp 136.40° C. (DSC); $^1$H NMR (400 MHz, $D_2O$) δ 3.52 (s, 6H, H-15 and H-17), 3.61 (s, 3H, H-16), 3.71 (s, 3H, H-18), 3.77 (s, 3H, H-21), 3.87 (s, 2H, H-20), 6.26 (d, J=12.1 Hz, 1H, H-8), 6.42 (s, 2H, H-10 and H-14), 6.43 (d, J=12.1 Hz, 1H, H-7), 6.70 (d, J=8.8 Hz, 1H, H-3), 6.79 (broad d, J=8.8 Hz, 1H, H-4), 7.16 (broad s, 1H, H-6); $^{13}$C NMR (100 MHz $\{^1H\}$, $D_2O$) δ 41.27 (C-20), 54.58 (C-21), 56.99 (2C, C-15, and C-17), 57.21 (C-18), 62.09 (C-16), 107.60 (2C, C-10 and C-14), 113.89 (C-3), 122.98 (C-6), 126.22 (C4), 130.25 (C-8), 130.69 (C-7), 131.37 (C-5), 134.61 (C-9), 137.09 (C-12), 142.42 (d, $^2J_{PC}$=6.9 Hz, C-1), 150.89 (d, $^3J_{PC}$=4.6 Hz, C-2), 153.33 (2C, C-11 and C-13), 169.95 (C-19). Anal. Calcd for $C_{21}H_{28}NO_{10}P$: C, 51.96; H, 5.81; N, 2.88; P, 6.38. Found: C, 51.74; H, 5.79; N, 2.87; P, 6.30.

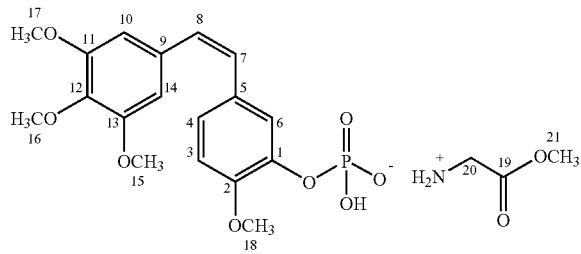

(Note: Numbering systems as shown above, and wherever such numbering systems are shown herein, are for convenience only and may not be consistent with IUPAC nomenclature).

Figure 12:
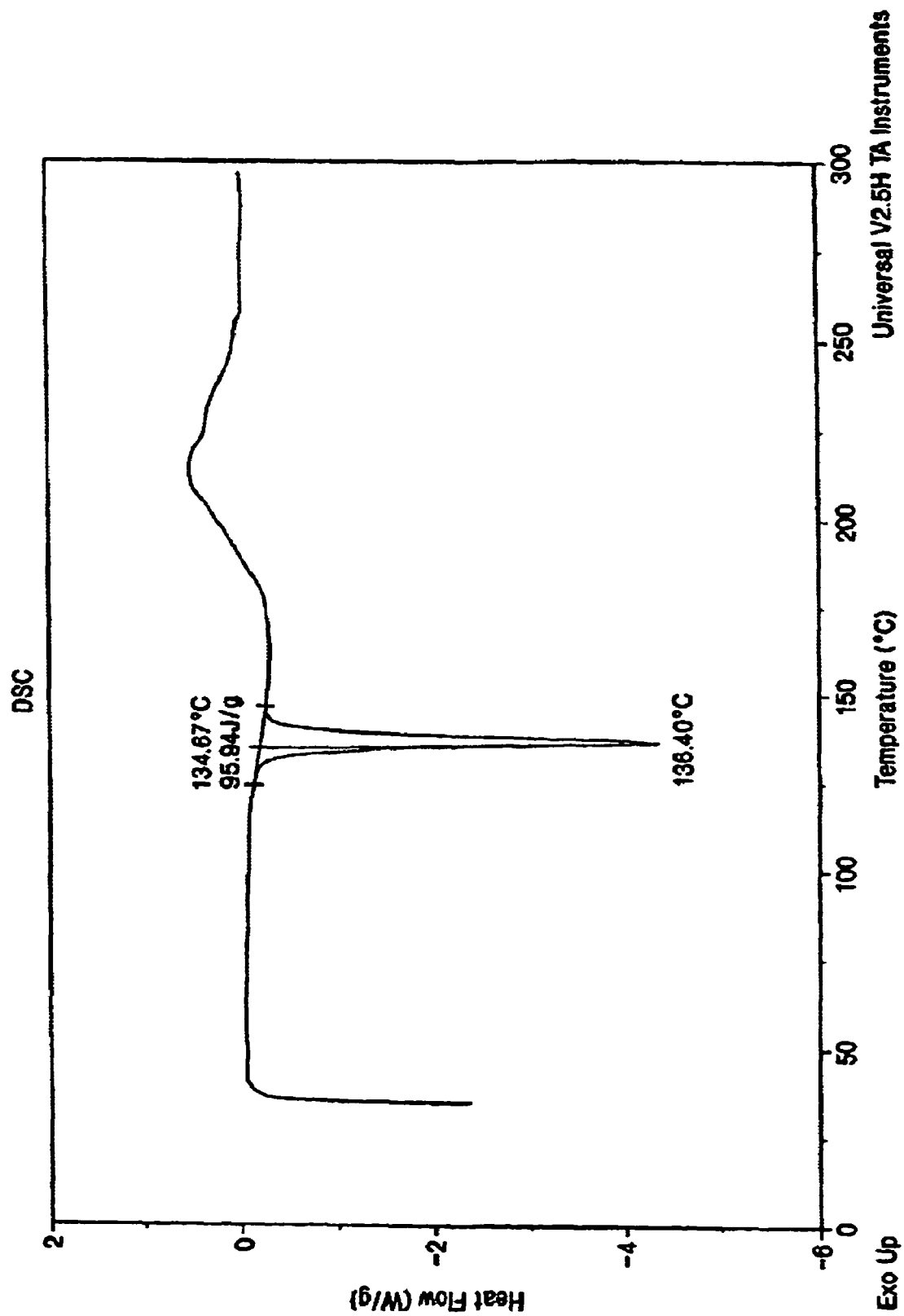
FIG. 12 shows the differential scanning calorimetry (DSC) thermogram of the CA4P monoglycine methyl ester salt (prepared in Example 4).
Figure 13:
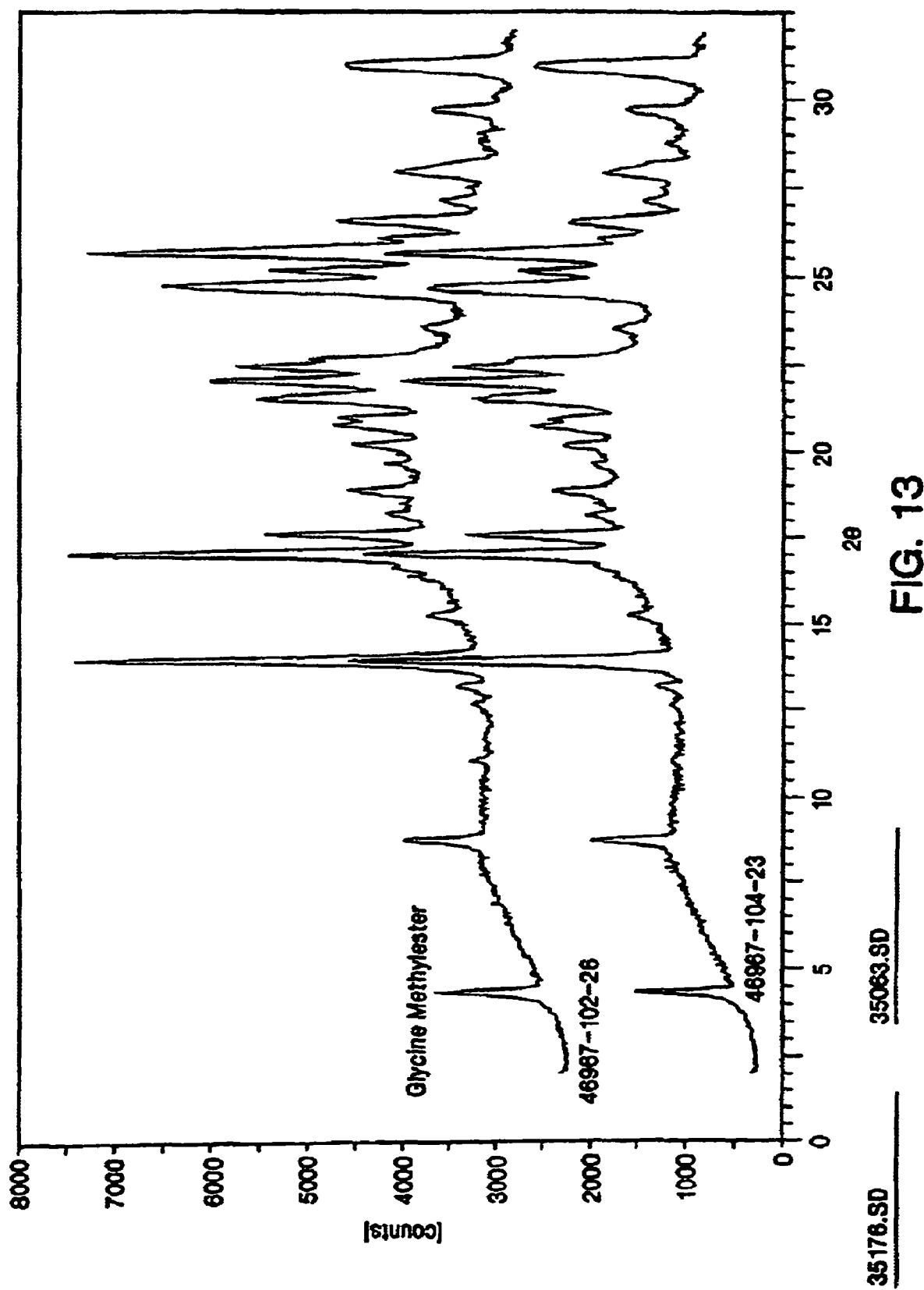
FIG. 13 shows the powder X-ray diffraction patterns of the CA4P monoglycine methyl ester salt (prepared in Example 4).

The DSC of the cis-CA4P monoglycine methyl ester salt (sample size: 3.7400 mg) is shown in FIG. 12; FIG. 13 shows the powder X-ray data for this material (2 batches).

Example 5

Preparation of the Glycine Ethyl Ester Salt of CA4P Free Acid

Ethyl acetate (2 mL), CA4P isopropanol solution (150 micro L of a 0.42 M solution, 63 micro mol) and glycine ethyl ester methyl tert-butyl ether solution (800 micro L of a 0.08 M solution, 64 micro mol) were added to an HPLC vial and agitated vigorously for ~3 minutes. The resulting clear solution was seeded with a drop of slurry from another experiment and the mixture was allowed to stand overnight at ambient temperature. A white solid formed that did not appear to be crystalline based upon microscopic examination and so the mixture was allowed to stand at ambient temperature for three more days. Methyl tert-butyl ether (1 mL) was added and the mixture was stirred for about 10 minutes. Microscopic examination of the resulting mixture indicated that the solid had converted to a crystalline needles. The needles were isolated by vacuum filtration and dried to afford the glycine ethyl ester salt of CA4P (22.4 mg, 66 M % yield). Proton NMR analysis indicated that the ratio of glycine ethyl ester to CA4P was 1.7:1. $^1$H NMR data for CA4P glycine ethyl ester.

$^1$H NMR (300 MHz, D$_2$O) δ1.20 (t, J=7.2 Hz, 3H, CH$_3$), 3.60 (s, 6H, H-15 and H-17), 3.66 (s, 3H, H-16), 3.74 (s, 3H, H-18), 3.79 (s, 2H, CH$_2$N), 4.21 (q, J=7.2 Hz, 2H, CH$_2$CH$_3$), 6.44 (d, J=12.2 Hz, 1H, H-8), 6.55 (d, J=12.2 Hz, 1H, H-7), 6.57 (s, 2H, H-10 and H-14), 6.80 (d, J=8.7 Hz, 1H, H-3), 6.85 (broad dl, J=8.7 Hz, 1H, H-4), 7.23 (broad s, 1H, H-6).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications and patent documents are cited herein, the disclosures of which are incorporated by reference in their entireties.

What is claimed is:

1. A crystalline form of combretastatin A4 phosphate mono-tromethamine.
2. The crystalline form of claim 1, wherein the olefin of the compound is in the cis configuration.
3. The crystalline form of claim 1 that has less than 1% water weight gain per weight of compound.
4. The crystalline form of claim 1, wherein the form is an achiral neat form (N–I), which does not contain any solvent sites.
5. The crystalline form of claim 1, wherein the differential scanning calorimetry thermogram shows a single melt exotherm at 196° C.
6. The crystalline form of claim 1, wherein thermogravimetric analysis does not show weight losses below 150° C.
7. The crystalline form of claim 1, wherein equilibrium aqueous solubility at 25° C. is 3.37 mg/mL at pH 4.8.
8. The crystalline form of claim 1 having a pH-solubility profile as shown in FIG. 4.
9. The crystalline form of claim 1 having a moisture sorption/desorption profile as shown in FIG. 1.

* * * * *